US006353151B1

(12) United States Patent
Leinwand et al.

(10) Patent No.: US 6,353,151 B1
(45) Date of Patent: Mar. 5, 2002

(54) TRANSGENIC MODEL FOR HEART FAILURE

(75) Inventors: Leslie A. Leinwand, Boulder, CO (US); Karen L. Vikstrom, Fayetteville, NY (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 08/938,105

(22) Filed: Sep. 26, 1997

Related U.S. Application Data

(60) Provisional application No. 60/026,742, filed on Sep. 26, 1996.

(51) Int. Cl.[7] ...................... A01K 67/00; A01K 67/027; C12N 15/63; G01N 33/00

(52) U.S. Cl. ............................. 800/18; 800/3; 800/13; 800/14; 435/320.1

(58) Field of Search ............................. 536/23.1; 800/8, 800/9, 13, 14, 18, 21, 22, 25, 3; 435/320.1

(56) References Cited

U.S. PATENT DOCUMENTS

| | | | |
|---|---|---|---|
| 4,736,866 A | 4/1988 | Leder et al. ................. | 800/10 |
| 5,387,742 A | 2/1995 | Cordell ........................ | 800/12 |
| 5,434,340 A | 7/1995 | Krimpenfort et al. ......... | 800/11 |
| 5,476,996 A | 12/1995 | Wilson et al. ................ | 800/10 |
| 5,487,992 A | 1/1996 | Capecchi et al. ............. | 435/6 |
| 5,489,742 A | 2/1996 | Hammer et al. .............. | 800/9 |
| 5,489,743 A | 2/1996 | Robinson et al. ............. | 800/3 |
| 5,491,283 A | 2/1996 | Groffen et al. ............... | 800/10 |
| 5,510,099 A | 4/1996 | Short et al. ................... | 800/3 |
| 5,512,281 A | 4/1996 | Ruprecht .................... | 424/93.6 |
| 5,523,226 A | 6/1996 | Wheeler ...................... | 435/325 |
| 5,530,177 A | 6/1996 | Bleck et al. .................. | 800/7 |
| 5,530,178 A | 6/1996 | Mak ............................ | 800/11 |
| 5,530,179 A | 6/1996 | Terhorst et al. ............... | 800/3 |
| 5,532,158 A | 7/1996 | Suzuki et al. ................ | 435/354 |
| 5,545,806 A | 8/1996 | Lonberg et al. ............... | 800/6 |
| 5,545,808 A | 8/1996 | Hew et al. .................... | 800/20 |

OTHER PUBLICATIONS

Wall, RJ Transgenic livestock: Progress and prospects for the future. Theriogenology 45: 57–68, 1996.*
Mullins et al. Fulminant hypertension in transgenic rats harboring the mouse Ren–2 gene. Nature 344: 541–544, Apr. 1990.*
Hammer et al. Spontaneous inflammatory disease in transgenic rats expressing HLA–B27 and human b2m: An animal model of HLA–B27–associated disorders. Cell 63: 1099–1112 Nov. 1990.*
Mullins et al. Expression of the DBA/2J Ren–2 gene in the adrenal gland of transgenic mice. EMBO J. 8: 4065–4072, 1989.*
Taurog et al. HLA–B27 in inbred and non–inbred transgenic mice. J. Immunol. 141: 4020–4023 Dec. 1988.*
Vickstrom et al. A murine model for hypertrophic cardiomyopathy. Zeitschrift fur Kardiologie 84 (Suppl. 4): 49–54 (abstract only), 1995.*
Vickstrom et al. (1994a) Transgenic mouse model for familial hypertrophic cardiomyopathy. Circulation 90, No. 4, Part 2: 1521 Oct. 1994.*
Vikstrom et al. (1994b) Transgenic mouse model for familial hypertrophic cardiomyopathy. Molec. Biol. of the Cell 5(Suppl.): 405A, 1994.*
Vikstrom et al. (1994c) Transgenic and cell culture models of muscle development and function. J. of Cell. Biochem. Supplement O (18D): 471, 1994.*
Vikstrom et al. Transgenic mouse model for hypertrophic cardiomyopathy. Molec. Biol. of the Cell 4(Suppl.): 39A, 1993.*
McNally et al. Complete nucleotide sequence of full length cDNA for rat alpha cardiac myosin heavy chain. Nucl. Acids Res. 17: 7527–7528, 1989.*
Rayment et al. Three–dimensional structure of myosin sub-fragment–1: A molecular motor. Science 261: 50–58, Jul. 1993.*
Vikstrom et al., *Zeitschrift Fur Kardiologie*, 84(4):49–54 (1995).
Vikstrom et al., *Curr Opin Cell Biol*, 8(1):97–105 (1996).
Bertin et al. (1993) *Cardiovascular Research* 27:1606–1612.
Chen et al (1992) *Biochemical and Biophysical Research Communications* 188(2):547–553.
Gaudin et al. (1995) *J. Clin. Invest.* 95:1676–1683.
Geisterfer–Lowrance et al. (1996) *Science* 272:731–734.
Iwase et al. (1996) *Circ Res.* 78:517–524.
Koch et al. (1995) *Science* 268:1350–1353.
Kurabayashi, et al. (1988) *J. Clin. Invest.* 82:524–531.
Milano et al. (1994) *Science* 264:582–586.
Milano et al. (1994) *Proc. Natl. Acad. Sci. USA* 91:10109–10113.
Milano et al. (1995) *J. Thorac. Cardiovasc. Surg.* 109:236–241.
Samama et al. (1997) *Proc. Natl. Acad. Sci. USA* 94:137–141.
Sweeney et al. (1994) *The Journal of Biological Chemistry* 269(2):1603–1605.
Tsika et al. (1990) *Proc. Natl. Acad. Sci. USA* 87:379–383.
Vikstrom et al. (1996) *Molecular Medicine* 2(5):556–567.
Dillman, W. (1996) *Molecular and Cellular Biochemistry* 157:125–128.
Eldin, P. et al. (1995) *Biochem J.* 306:345–351.
Geisterfer–Lowrance, A.A.T., et al. (1990) *Cell* 62:999–1006.
Palermo, J., (1996) *Circulation Research* 78(3):504–509.

* cited by examiner

*Primary Examiner*—Deborah Crouch
*Assistant Examiner*—Anne-Marie Baker
(74) *Attorney, Agent, or Firm*—Fulbright & Jaworski

(57) ABSTRACT

The present invention discloses a transgenic mouse that is a model for congestive heart failure. The disclosed mouse is a subset of a transgenic mouse line that is a model for hypertrophic cardiomyopathy. Also disclosed are a recombinant nucleic acid molecule encoding a transgene, and methods of using the transgenic mouse model to study congestive heart failure and conditions and treatments related thereto.

37 Claims, 1 Drawing Sheet

TRANSGENIC MODEL FOR HEART FAILURE

CROSS-REFERENCE TO RELATED APPLICATIONS

The present application claims priority from U.S. Provisional Application Ser. No. 60/026,742, filed Sep. 26, 1996.

GOVERNMENT RIGHTS

This invention was made in part with government support under a National Institutes of Health merit award, and training grant PHS5T32HL07271, awarded by the National Institutes of Health. The government has certain rights to this invention.

FIELD OF THE INVENTION

The present invention relates to a transgenic animal model for studying heart failure. In particular, the present invention relates to methods of studying molecular/cellular events associated with congestive heart failure, of testing drug candidates for prevention or treatment of congestive heart failure, of studying the effects of factors such as diet or exercise on congestive heart failure, and of studying specific conditions or diseases associated with congestive heart failure.

BACKGROUND OF THE INVENTION

A variety of human diseases and conditions which are manifested by cardiac abnormalities or cardiac dysfunction can lead to heart failure. Heart failure is a physiological condition in which the heart fails to pump enough blood to meet the circulatory requirements of the body. The study of such a condition in genetically diverse humans is difficult and unpredictable. Therefore, there is a need for a model system which facilitates the study of the mechanisms and causes of heart failure as well as the identification of potential therapeutic targets.

The development of transgenic animal technology has provided significant advances for obtaining more complete information about complex systems in vivo. By manipulating the expression of gene(s) in vivo, it is possible to gain insight into the roles of such genes in a particular system or to study aspects of the system in a genetically controlled environment. Although cardiac disease in a small mammal is inherently different from that seen in humans, mammals such as the mouse allow analysis of disease at molecular and cellular levels that is often impossible in humans.

Accordingly, it is an objective of the present invention to provide a transgenic model system for the study of heart failure and methods of use thereof.

SUMMARY OF THE INVENTION

One embodiment of the present invention is a transgenic mouse which is a model for studying congestive heart failure. Such a transgenic mouse has incorporated into its genome a transgene which includes: (a) a heart tissue-specific promoter; and, (b) a nucleic acid sequence encoding an amino acid sequence of a α myosin heavy chain protein. The nucleic acid sequence has a first mutation comprising a point mutation which results in an Arg403Gln mutation in the amino acid sequence, and a second mutation comprising an interstitial deletion in a portion of the nucleic acid sequence that encodes an actin binding domain. The transgene is expressed in the heart tissues of the transgenic mouse.

Another embodiment of the present invention relates to a transgenic mammal which is a model for congestive heart failure. Such a transgenic mammal has substantially the same transgene incorporated into its genome as is described above for a transgenic mouse of the present invention.

Yet another embodiment of the present invention relates to a recombinant nucleic acid molecule which includes a nucleic acid sequence encoding an amino acid sequence of an α myosin heavy chain protein, such nucleic acid sequence being operatively linked to one or more expression control sequences. The nucleic acid sequence has a first mutation comprising a point mutation which results in an Arg403Gln mutation in the amino acid sequence and a second mutation comprising an interstitial deletion in a portion of the nucleic acid sequence that encodes an actin binding domain.

Yet another embodiment of the present invention relates to a method for studying the molecular and cellular events associated with congestive heart failure comprising the steps of: (a) harvesting cells and tissues from a transgenic mouse of the present invention as described above; and, (b) comparing the cells and tissues from the transgenic mouse to cells and tissues from a mouse which does not carry the transgene in an assay. Such an assay is selected from the group of morphological examination of cardiac cells; histological examination of coronary vessels; histological examination of heart sections; histological examination of myocytes; histological examination of myofibrils; evaluation of cardiac myocyte DNA replication and expression; evaluation of cardiac-related enzyme activity; and evaluation of apoptosis of cardiac cells.

Another embodiment of the present invention relates to a method to identify compounds for treating congestive heart failure. Such a method includes the steps of: (a) administering a compound to be evaluated to a transgenic mouse of the present invention as described above; and, evaluating physiological and pathological changes in the transgenic mouse compared to a mouse that did not receive the compound to determine the efficacy of the compound for treating congestive heart failure.

Yet another embodiment of the present invention relates to a method for evaluating the effects of external factors selected from the group of diet and exercise on congestive heart failure. Such method includes the steps of (a) establishing a normal control regimen for an external factor in a first transgenic mouse of the present invention as described above; (b) modulating the regimen for the external factor in a second transgenic mouse of the present invention as described above; and (c) monitoring the second transgenic mouse for a change in a characteristic associated with congestive heart failure compared to the first transgenic mouse.

Another embodiment of the present invention relates to a method to study the molecular and cellular events connected with a condition associated with congestive heart failure. Such a method includes the steps as described above for the method to study the molecular and cellular events connected with congestive heart failure. Such a condition or disease includes, but is not limited to dilated cardiomyopathy, hypertrophic cardiomyopathy, acute aortic regurgitation, tricuspid stenosis, constrictive pericarditis, acute infective endocarditis, ischemia heart disease, hypertension, primary myocardial disease, valvular disease, pericardial disease, hyperthyroidism, anemia, arteriovenous fistula, beriberi and Paget's disease.

Another embodiment of the present invention relates to a method to produce a transgenic mouse which is a model for heart failure. Such a method includes the steps of (a) producing a first transgenic mouse of the present invention as described above; (b) producing a second transgenic mouse having incorporated into its genome a transgene comprising a nucleic acid sequence encoding a protein selected from the group of a protein involved in the angiotensin system, a protein involved in the β adrenergic pathway and a protein involved in calcium handling systems; and (c) breeding the first transgenic mouse with the second transgenic mouse to produce a third transgenic mouse that is useful for studying heart failure. In a preferred embodiment, the second transgenic mouse has a transgene encoding a $\beta_1$-adrenergic receptor.

Yet another embodiment of the present invention relates to a method to produce a transgenic mouse that is a model for studying congestive heart failure. Such a method includes the steps of (a) introducing into an embryonic cell of a mouse a transgene as described previously herein; and (b) obtaining progeny having the transgene stably incorporated into the genome, such transgene being expressed in the heart tissues of the progeny. Such a method can further include step (c) of selecting male transgenic progeny, and further include the step of selecting male transgenic progeny that are at least about 5 months of age.

Another embodiment of the present invention relates to a transgenic mouse that is a model for hypertrophic cardiomyopathy. Such a mouse has incorporated into its genome a transgene comprising (a) a heart tissue-specific promoter; and, (b) a nucleic acid sequence encoding an amino acid sequence of a α myosin heavy chain protein. The nucleic acid sequence has a first mutation comprising a point mutation which results in an Arg403Gln mutation in the amino acid sequence and a second mutation comprising an interstitial deletion in a portion of the nucleic acid sequence that encodes an actin binding domain. The transgene is expressed in the heart tissues of the transgenic mouse at a level sufficient to promote hypertrophic cardiomyopathy in the mouse. In this embodiment, such a transgenic mouse is preferably a female transgenic mouse, or a male transgenic mouse that is at least less than about 8 months of age.

DETAILED DESCRIPTION OF THE INVENTION

Figure 1:
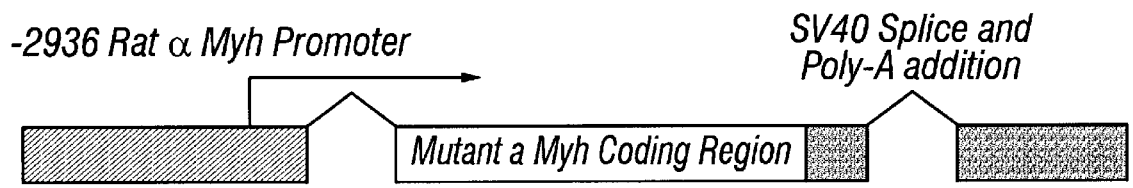
FIG. 1 is a schematic drawing of the mutant α myosin heavy chain transgene of the present invention.

The present invention generally relates to a transgenic model for heart failure and methods to use such model for the study of heart failure. Transgenic mice of the present invention were constructed by the present inventors as a model for studying hypertrophic cardiomyopathy. Accordingly, it is one embodiment of the present invention to provide a transgenic mouse model for hypertrophic cardiomyopathy. It was unexpectedly found that older males of these mice uniformly exhibit particular phenotypic characteristics which are associated with congestive heart failure. The present invention is generally directed to the use of such transgenic mice as a model to study various aspects of congestive heart failure.

Prior to the present invention, a mouse model of hypertrophic cardiomyopathy (HCM) was described which mimics several aspects of HCM in humans, namely the appearance of myocellular disarray, fibrosis, and cardiac dysfunction (Geisterfer-Lowrance et al., 1996, *Science*, 272:731–734). However, while this mouse model for HCM genetically most closely resembles the human disease, phenotypically it displays at least one substantial difference, namely profound left atrial enlargement in the absence of ventricular hypertrophy, features not typically seen in the human condition. Consequently, these animals are not suitable for studying many aspects of HCM pathogenesis. Moreover, the previously described transgenic mouse models of HCM are not also models of congestive heart failure.

The present inventors have created the first transgenic mouse lines which phenotypically are virtually identical to human HCM and allow the impact of contractile protein mutations on the heart to be analyzed and factors contributing to the disease's natural history to be determined. In addition, the present inventors have created the first transgenic mouse lines which are a model for congestive heart failure.

The transgenic mice of the present invention and methods of using these mice provide insight into the basic mechanisms underlying congestive heart failure and cardiac hypertrophy. In addition, the knowledge gained from studying cardiac pathogenesis in the transgenic mice of the present invention will impact knowledge of human congestive heart failure and human HCM. The power of using a combined molecular and morphological analysis of the transgenic mice of the present invention and the ability to breed them with other genetically altered mouse lines will facilitate the search for the elements involved in the pathogenesis of congestive heart failure and HCM and the identification of potential therapeutic targets.

One embodiment of the present invention is a transgenic mouse which is a model for studying congestive heart failure. Such a transgenic mouse has incorporated into its genome a transgene which includes: (a) a heart tissue-specific promoter; and, (b) a nucleic acid sequence encoding an amino acid sequence of a α myosin heavy chain protein. The nucleic acid sequence has a first mutation comprising a point mutation which results in an Arg403Gln mutation in the amino acid sequence, and a second mutation comprising an interstitial deletion in a portion of the nucleic acid sequence that encodes an actin binding domain. The transgene is expressed in the heart tissues of the transgenic mouse. As will be discussed in detail below, older, male transgenic mice of the present invention are suitable models for congestive heart failure, whereas female transgenic mice are not suitable models for congestive heart failure. It is to be understood, however, that female transgenic mice of the present invention are included in this embodiment of the invention, because female transgenic mice may be useful models for studying congestive heart failure (i.e., for studying factors associated with resistance to development of heart failure, such as the effect of hormones). In addition, female transgenic mice of the present invention may be useful as control animals to which male transgenic mice that are models of congestive heart failure can be compared. Of course, the female transgenic mice of the present invention are also important as breeders for propagating the transgenic line.

According to the present invention, a transgenic mouse is a mouse which includes a recombinant nucleic acid molecule (i.e., transgene) that has been introduced into the genome of the mouse at the embryonic stage of the mouse's development. As such, the transgene will be present (i.e., incorporated into) in all of the germ cells and somatic cells of the mouse. Methods for the introduction of a transgene into a mouse embryo are known in the art and are described in detail in Hogan et al., "Manipulating the Mouse Embryo. A Laboratory Manual", Cold Spring Harbor press, Cold Spring Harbor, N.Y., 1986, which is incorporated by reference herein in its entirety. Many U.S. patents also describe production of a transgenic animal (See for example, Leder et al., U.S. Pat. No. 4,736,866, 1988; Cordell, U.S. Pat. No. 5,387,742, 1995; Lonberg et al., U.S. Pat. No. 5,545,806, 1996; Capecchi et al., U.S. Pat. No. 5,487,992, 1996; Hammer et al., U.S. Pat. No. 5,489,742, 1996; Bleck et al., U.S. Pat. No. 5,530,177, 1996; Wheeler, U.S. Pat. No. 5,523,226, 1996; Robinson et al., U.S. Pat. No. 5,489,743, 1996; Krimpenfort et al., U.S. Pat. No. 5,434,340, 1995; and Terhorst et al., U.S. Pat. No. 5,530,179, 1996; all of which are incorporated by reference herein in their entirety). For example, a recombinant nucleic acid molecule (i.e., transgene) can be injected into the male pronucleus of a fertilized mouse egg to cause one or more copies of the recombinant nucleic acid molecule to be retained in the cells of the developing mouse. A mouse retaining the transgene, also called a "founder" mouse, usually transmits the transgene through the germ line to the next generation of mice, establishing transgenic lines. According to the present invention, a transgenic mouse also includes all progeny of a transgenic mouse that inherit the transgene.

As used herein, a transgene-negative littermate is a mouse which is born into the same litter as a transgenic mouse described herein (i.e., a littermate), but did not inherit the transgene (i.e., is transgene-negative, or does not have the transgene incorporated into its genome). Such a mouse is essentially a normal, or wild-type, mouse and is useful as an age-matched control for the methods described herein.

According to the present invention, any non-human animal suitable for the study of heart failure may be used as a starting organism for the derivation of a transgenic animal of the present invention. Preferably, a transgenic model of the present invention is a mammal including, but not limited to, rabbits, primates and rodents. Most preferably, a transgenic model of the present invention is a rodent, and even more preferably, a mouse. It is an embodiment of the present invention that the transgene, methods and applications for using a transgenic mouse of the present invention as described below in detail can be modified and applied to any suitable transgenic animal for the study of heart failure.

As used herein, the condition referred to as congestive heart failure is the pathophysiological state in which an abnormality of cardiac function is responsible for the failure of the heart to pump enough blood to meet the circulatory requirements of the body. According to the present invention, congestive heart failure can be characterized by at least one of the following phenotypic characteristics: dilation (dilatation), systolic dysfunction, and heart wall thinning.

According to the present invention, congestive heart failure can be the end-stage event, or secondary condition, of a variety of cardiac diseases and conditions, including, but not limited to dilated cardiomyopathy, hypertrophic cardiomyopathy, acute aortic regurgitation, tricuspid stenosis, constrictive pericarditis, acute infective endocarditis, ischemia heart disease, hypertension, primary myocardial disease, valvular disease, pericardial disease, hyperthyroidism, anemia, arteriovenous fistula, beriberi and Paget's disease. Each of these diseases and conditions may be associated with different or the same phenotypic characteristics as described above for congestive heart failure.

As used herein, the condition referred to as hypertrophic cardiomyopathy (HCM) is a clinically heterogenous disease of the heart with a dominant mode of inheritance which is characterized by thickening of the muscular walls in the ventricular septum and left ventricle (cardiac hypertrophy), resulting in a narrowing of the left ventricle outflow tract. More particular characteristics of hypertrophic cardiomyopathy include myocyte hypertrophy, myocellular disarray, interstitial fibrosis, small vessel coronary disease, and in some cases left ventricular outflow tract obstruction. The potential for understanding the pathogenesis of human HCM has advanced with the identification of mutations in the $\beta$ myosin heavy chain (Myh) gene in two kindreds with HCM. 40 $\beta$ myosin heavy chain mutations, primarily in the "motor" domain of the molecule, have been reported. The identification of mutations in additional muscle structural proteins (cardiac troponin T, $\alpha$-tropomyosin and cardiac myosin binding protein C) has shown that HCM is also genetically heterogenous and led to the hypothesis that HCM is also genetically heterogenous and led to the hypothesis that HCM is a disease of the sarcomere. Although the genetic evidence for contractile protein defects in HCM is unequivocal, the link between these mutations and the clinical phenotype remains unclear. The dominant mode of inheritance may imply that the mutant protein acts as a dominant negative, interfering with the function of the wild-type protein. Several lines of evidence support this hypothesis. Myosin purified from HCM patients (which is a mixture of wild-type and mutant protein) exhibits decreased motility in in vitro motility assays. Biochemical analysis of a mutant allele (Arg403Gln) demonstrates a defect in actin-activated ATPase activity and decreased motility in an in vitro assay. In addition, the mutant myosin heavy chain exhibits a dominant effect when mixed with wild-type protein, disproportionately slowing the velocity of the mixture.

Hypertrophic cardiomyopathy is distinguished from congestive heart failure in that although hypertrophic cardiomyopathy can lead to the secondary condition of congestive heart failure, hypertrophic cardiomyopathy is not the only cause of congestive heart failure. More particularly, congestive heart failure is characterized by phenotypic traits that are not typically associated with hypertrophic cardiomyopathy, such as dilation, wall thinning, and systolic dysfunction. Older, adult male transgenic mice of the present invention which are suitable models for congestive heart failure exhibit all of such phenotypic traits.

In one embodiment, transgenic mice of the present invention are useful as models for hypertrophic cardiomyopathy. In another embodiment, a subset of such mice are useful as models for congestive heart failure. The present invention is primarily directed toward such a subset of transgenic mice which are models for congestive heart failure. In particular, transgenic mice of the present invention which are suitable models for congestive heart failure can be identified by criteria which include sex, age, and level of expression of the transgene. Such mice develop phenotypic characteristics of heart failure, including dilation, systolic dysfunction, and wall thinning, each of which are described in detail below.

A transgenic mouse of the present invention has incorporated into its genome a transgene. As used herein, a transgene is a recombinant nucleic acid molecule that has been introduced into the genome of the mouse at the embryonic stage of the mouse's development. A transgene that has been incorporated into the genome of an animal is a recombinant nucleic acid molecule that has stably integrated into the DNA of all of the germ cells and somatic cells in an animal. A transgene typically also includes regulatory sequences, such as expression control sequences (e.g., promoters), which control the expression of the transgene in the cells of the animal. Such sequences are described in detail below.

In the transgenic mouse described herein, the transgene includes (a) a heart tissue-specific promoter; and (b) a nucleic acid sequence encoding an amino acid sequence of an α myosin heavy chain protein. The nucleic acid sequence contains two mutations: (1) a point mutation, wherein a guanine base at position 1445 is substituted with an adenine base, such substitution resulting in an amino acid substitution of an arginine with a glutamine at amino acid position 403 (Arg403Gln); and (2) an interstitial deletion in the portion of DNA encoding amino acids within the actin binding domain. An α myosin heavy chain cDNA having the above described mutations is also referred to herein as a mutant α myosin heavy chain (Myh), or a mutant α Myh.

An α myosin heavy chain gene which has been mutated as described herein is preferably used as the transgene in the production of a transgenic mouse of the present invention, although it is within the scope of the present invention to use the β myosin heavy chain in the production of a different (i.e., non-mouse) transgenic mammal. In contrast to humans, where β myosin heavy chain is the predominant cardiac myosin isoform, α myosin heavy chain is the predominant isoform of the adult mouse ventricle. Therefore, a mutant rat α myosin heavy chain cDNA was selected by the present inventors to construct the transgene coding region of the transgenic mouse disclosed herein. It is within the scope of the present invention, however, to use any mammalian α myosin heavy chain gene for the production of a transgenic mammal of the present invention. The α myosin heavy chain is highly conserved between mammalian species. Rat and mouse α myosin heavy chain are 98.9% identical at the amino acid level (22 differences out of 1938 amino acids) with the differences being similar to the neutral polymorphisms found between various inbred mouse strains. In addition, the α myosin heavy chain amino acid sequence is from about 96.9% to about 98.7% identical between rat, mouse and human. Moreover, the arginine at position 403 of the amino acid sequence of the wild-type α myosin heavy chain protein is conserved between rat, mouse and human, suggesting that this amino acid residue is conserved among many mammalian species. If a transgenic mammal other than a rat or mouse is produced (e.g., a pig or a primate), an α myosin heavy chain gene from the desired species is preferably used. Knowing the nucleic acid sequences rat and mouse α myosin heavy chain nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain α myosin heavy chain nucleic acid molecules for other mammals. Such nucleic acid molecules can be obtained in a variety of ways including screening appropriate expression libraries with antibodies directed against α myosin heavy chain; traditional cloning techniques using oligonucleotide probes from conserved regions of the α myosin heavy chain to screen appropriate libraries or DNA; and PCR amplification of appropriate libraries or DNA using oligonucleotide primers. Methods of producing mutated α myosin heavy chain nucleic acid sequences are discussed in detail below.

As discussed above, one of the mutations in a mutant a myosin heavy chain transgene of the present invention is an interstitial deletion which results in a deletion of amino acids within the actin binding domain of the α myosin heavy chain. Such an interstitial deletion results in at least about a 15 amino acid deletion, and more preferably, at least about a 30 amino acid deletion, and even more preferably, at least about a 45 amino acid deletion, and even more preferably, at least about a 60 amino acid deletion within the actin binding domain of an α myosin heavy chain. Such an interstitial deletion, in conjunction with the above-described point mutation, Arg403Gln, preferably inhibits the binding of actin to the actin binding domain of the α myosin heavy chain. More particularly, such a deletion, in conjunction with the above-described point mutation encodes a mutant α myosin heavy chain which, when expressed in male transgenic mice of a particular age range and having a transgene expression level as described herein, results in such mouse having the phenotypic characteristics of congestive heart failure as described in detail below.

In one embodiment of the present invention, a deletion in an actin binding domain comprises the deletion of amino acids from about position 468 to about position 527. It is another embodiment of the present invention that such a deletion of amino acids can include deletion of a portion of the putative actin binding domain that is less than or greater than the region defined by amino acids 468 to 527, if the characteristics of the transgenic mouse having phenotypic characteristics of congestive heart failure of the present invention, as described herein, are maintained or enhanced.

Such an interstitial deletion in the actin binding domain is preferably bridged by the addition of a nucleic acid sequence encoding an addition of amino acid residues that do not encode a portion of the actin binding domain. In other words, the amino acid sequence of the addition of amino acid residues is not selected from a sequence of amino acid residues that is naturally found within the actin binding domain of the α myosin heavy chain. Preferably, such an addition of amino acid residues comprises an amino acid sequence of about eight amino acids. In one embodiment, such an addition of residues is the sequence, SerSerLeuProHisLeuLysLeu, represented herein as SEQ ID NO:1.

In one embodiment of the present invention, a transgene used to produce a transgenic mouse of the present invention has a nucleic acid sequence encoding a mutant α myosin heavy chain that is represented herein by SEQ ID NO:2. Such a nucleic acid sequence encodes an amino acid sequence represented herein as SEQ ID NO:3.

The transgene used to produce a transgenic mouse of the present invention also has a heart tissue-specific promoter. According to the present invention, a heart tissue-specific promoter is a promoter that drives expression of the transgene exclusively, or substantially exclusively, in the heart. Examples of such a promoter include, but are not limited to α myosin heavy chain promoter and myosin light chain 2V (ventricular) promoter. Preferably, the promoter is an α myosin heavy chain promoter which is operatively linked to the mutant α myosin heavy chain nucleic acid sequence. In one embodiment, a promoter for use in a recombinant nucleic acid molecule of the present invention is an α myosin heavy chain promoter. If the recombinant nucleic acid molecule is to be used in the production of a transgenic mouse or rat, it is preferable to use a mouse or rat α myosin heavy chain promoter.

The phrase "operatively linked" refers to insertion of nucleic acid sequences, including the expression control sequences, in a manner such that the molecule is able to be expressed in cardiac cells when integrated into a host genome. Expression control sequences are regulatory sequences that are compatible with the transgenic host's cells and that control the expression of the nucleic acid molecule of the present invention. In particular, expression control sequences control the initiation, elongation, and termination of transcription. Particularly important expression control sequences are those which control transcription initiation, such as promoter and enhancer sequences. Suitable expression control sequences include any expression control sequence that can function in at least one of the transgenic mammals of the present invention. A variety of such expression control sequences are known to those skilled in the art. Expression control sequences of the present invention can also include naturally occurring expression control sequences naturally associated with an α myosin heavy chain nucleic acid sequence. Suitable expression control sequences include any expression control sequence that can function in the transgene expression system of the present invention.

The mutant α myosin heavy chain transgene is constructed and cloned by standard methods known in the art. A mutated α myosin heavy chain transgene of the present invention can be constructed, for example, using recombinant DNA technology (e.g., polymerase chain reaction (PCR) amplification, cloning) or chemical synthesis. As used herein, a nucleic acid sequence can include the sense strand as well as the nonsense, strand, or complement of such nucleic acid sequence. Nucleic acid sequences can be modified using a variety of techniques including, but not limited to, classic mutagenesis techniques and recombinant DNA techniques such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Such standard methods are disclosed, for example, in Sambrook et al., 1989, *Molecular Cloning: A Laboratory Manual*, Cold Spring Harbor Labs Press. The reference Sambrook et al., ibid., is incorporated by reference herein in its entirety.

More particularly, the α myosin heavy chain transgene incorporating the mutations as disclosed above is ligated into a prokaryotic cloning vector. Prokaryotic cloning vectors and methods for using such vectors to clone DNA are well known in the art. The transgene is constructed to include both the mutant α myosin heavy chain gene described above and a heart tissue-specific promoter. Further, the transgene can include 5' and 3' flanking introns, and polyadenylation sequences.

Transgene sequences are cloned using a standard prokaryotic cloning system, and the transgene products are excised from the prokaryotic vector, purified, and injected into the pronuclei of fertilized mouse eggs. Stable integration of the transgene into the genome of the transgenic embryos allows permanent transgenic mouse lines to be established.

In a preferred embodiment, a transgene of the present invention includes a mutant α myosin heavy chain cDNA as described herein; approximately 2936 base pairs of rat α myosin heavy chain 5'-flanking region as a promoter; a hybrid intron at the 5' end of the mutant cDNA, comprising the 113 base pair fragment flanked by HindIII and EcoRI restriction endonucleases sites which is derived from the mammalian expression construct pMT21 (Genetics Institute, Cambridge, Mass.); the SV40 small t intron at the 3' end of the mutant cDNA; and SV40 small t polyadenylation sequences.

Mouse strains which are suitable for the derivation of transgenic mice as described herein are any common laboratory mouse strain. A preferred mouse strain to use for the derivation of transgenic mice founders of the present invention are (CBA X C57BL/6)F1 crosses. Preferably, founder mice of this cross are bred onto C57BL/6 mice to create lines of transgenic mice.

Transgenic mice of the present invention which are suitable models for congestive heart failure are adult male transgenic mice. Male and female transgenic mice of the present invention are suitable models for hypertrophic cardiomyopathy, but female transgenic mice are not suitable models for congestive heart failure, because female transgenic mice do not develop the phenotypic characteristics of congestive heart failure as described below. It is to be understood, however, that female transgenic mice of the present invention are suitable models for studying heart failure in conjunction with the male transgenic mice of the present invention, because the female mice are useful for studying resistance to heart failure and the a environmental/gender-related factors which contribute to resistance or susceptibility to congestive heart failure.

Transgenic mice of the present invention which are suitable models for congestive heart failure include male transgenic mice which are at least about 5 months of age. Preferably, such mice are at least about 6 months of age, and more preferably, at least about 7 months of age, and most preferably, at least about 8 months of age.

The above-described transgene is expressed in the heart tissues of transgenic mice of the present invention. In particular, the transgene is expressed in the heart tissues of transgenic mice at a level sufficient to promote congestive heart failure if the transgenic mouse is a male of at least about 5 months of age. In a transgenic mouse of the present invention which is a suitable model for congestive heart failure, the level of mutant α myosin heavy chain mRNA is preferably at least about 25% of the endogenous α myosin heavy chain mRNA level. More preferably, the level of mutant α myosin heavy chain mRNA is at least about 35%, and more preferably at least about 45%, and even more preferably, at least about 55% of the endogenous α myosin heavy chain mRNA level. It is noted that there is not a significant difference in the level of expression of the transgene between male and female transgenic mice of the present invention (i.e., males do not express significantly more or less transgene than females). The level of mutant α myosin heavy chain mRNA can be measured by any means of measuring MRNA levels known in the art. Such methods include, for example, Northern blots and RNAse protection assays. The interstitial deletion mutation in the transgene allows the transgene mRNA to be distinguished electrophoretically from the endogenous α myosin heavy chain mRNA.

In a transgenic mouse of the present invention which is a suitable model for congestive heart failure, mutant α myosin heavy chain protein comprises at least about 1% of the total myosin protein in the heart by mass. Preferably, the mutant α myosin heavy chain protein comprises at least about 3% by mass, and more preferably, at least about 9% by mass, and even more preferably, at least about 12% by mass of the total myosin protein in the heart. The amount of mutant α myosin heavy chain protein in a transgenic mouse or transgenic mammal of the present invention can be determined by any means for quantifying protein amount. Such methods include, for example, immunoblot assays. Quantitation can be by way of a densitometry measurement, for example. As discussed below in Example 1, the interstitial deletion mutation allows the transgene protein to be distinguished electrophoretically from the endogenous α myosin heavy chain.

Transgenic mice of the present invention which are suitable models for congestive heart failure display particular phenotypic characteristics associated with heart failure. As used herein, a phenotypic characteristic is an measurable or observable characteristic which results from the interaction of the genetic constitution of the mouse with its environment. Examples of phenotypic characteristics associated with heart failure are described below.

A phenotypic characteristic of transgenic mice of the present invention which are suitable models for congestive heart failure is dilation of the heart chambers. As used herein, dilation, also referred to as dilatation, is described as an enlarging or expanding of the heart chamber. In particular, such mice exhibit dilation of the left ventricle, although dilation of other chambers of the heart can occur. Dilation can be assessed by direct measurement of a heart obtained by necropsy or of a beating heart inside an organism by echoradiography. Such a measurement by echoradiography is termed left ventricular end-diastolic dimension, or LVEDD. According to the present invention, an adult transgene-negative mouse has an LVEDD of between about 1.8 mm and about 2.7 mm. A transgenic mouse of the present invention which is a suitable model for congestive heart failure has an LVEDD of between about 2.7 mm and about 4.0 mm.

Another phenotypic characteristic of transgenic mice of the present invention which are suitable models for congestive heart failure is that such mice exhibit thinning of the heart walls, also referred to herein as wall thinning. According to the present invention, the heart walls of a transgenic mouse which is a suitable model for congestive heart failure are at least about 10% thinner, and more preferably at least about 30% thinner, and even more preferably at least about 50% thinner, and most preferably at least about 70% thinner than the heart walls of a transgene-negative mouse. As such, transgenic mice of the present invention which are suitable models for congestive heart failure do not display, or alternatively, no longer display, cardiac hypertrophy. As used herein, cardiac hypertrophy refers to the distention or enlargement of the walls of the heart due to the amplification of its component cells, but not due to a quantitative increase in cells or new growth. Transgenic mice of the present invention which are suitable models for congestive heart failure have lost the hypertrophic characteristic if such characteristic was exhibited at a younger age. The overall dimensions of the heart of these mice may be greater than those of transgene-negative littermates, however, such enlargement would be due to dilation, as described above.

Yet another phenotypic characteristic of transgenic mice of the present invention which are suitable models for congestive heart failure is systolic dysfunction. As used herein, systolic dysfunction is a dysfunction in the contractile process of the heart which is characterized by an inability to expel sufficient blood. Systolic function can be assessed in mice by measuring the percentage fractional shortening (%FS), which is a measure of the shortening of the left ventricular minor axis during systole. Transgene-negative mice of the present invention typically have systolic function of between about %FS=50 and about %FS=60, whereas transgenic mice of the present invention which are suitable models for heart failure have significantly reduced systolic function of between about %FS=18 and about %FS=30.

Another embodiment of the present invention relates to a transgenic mammal which is a model for studying congestive heart failure. Such a transgenic mammal has incorporated into its genome a transgene comprising: (a) a heart tissue-specific promoter; and (b) a nucleic acid sequence encoding an amino acid sequence of an α myosin heavy chain protein. The nucleic acid sequence has the first and second mutations as described above for a transgenic mouse of the present invention, such transgene being expressed in the heart tissues of the transgenic mammal. In preferred embodiments, suitable mammals for use in the production of a transgenic mammal of the present invention include, but are not limited to, mice, rats, rabbits, sheep, pigs, cattle, and primates.

One embodiment of the present invention relates to a recombinant nucleic acid molecule comprising a nucleic acid sequence encoding an amino acid sequence of an α myosin heavy chain protein, such nucleic acid sequence being operatively linked to one or more expression control sequences. The nucleic acid sequence has a first mutation comprising a point mutation which results in an Arg403Gln mutation in the amino acid sequence; and a second mutation comprising an interstitial deletion in a portion of the nucleic acid sequence that encodes an actin binding domain. Such a nucleic acid sequence has been described in detail herein. A preferred expression control sequence for use in a recombinant nucleic acid molecule of the present invention is a heart tissue-specific promoter. Such promoters have been described in detail herein. According to the present invention, when a recombinant nucleic acid molecule is incorporated into the genome of an animal at the embryonic stage, the terms "recombinant nucleic acid molecule" and "transgene" can be used interchangeably. Preferred and alternative embodiments of such a recombinant nucleic acid molecule are those described above for a transgene of a transgenic mouse of the present invention.

It may be appreciated by one skilled in the art that use of recombinant DNA technologies can improve expression of transgenes disclosed herein by manipulating, for example, the number of copies of the nucleic acid molecules integrated into a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, substitutions or modifications of expression control signals (e.g., promoters, operators, enhancers), substitutions or modifications of translational control signals (e.g., ribosome binding sites, Shine-Dalgarno sequences) and deletion of sequences that destabilize transcripts.

It is to be noted that the term "a" or "an" entity refers to one or more of that entity; for example, a characteristic refers to one or more characteristics or at least one characteristic. As such, the terms "a" (or "an"), "one or more" and "at least one" can be used interchangeably herein. It is also to be noted that the terms "comprising", "including", and "having" can be used interchangeably.

One embodiment of the present invention is a method to study the molecular and cellular events associated with congestive heart failure. Such a method comprises the use of a transgenic mouse having phenotypic characteristics of congestive heart failure of the present invention. Specifically, a transgenic mouse of the present invention that is a suitable model for heart failure as defined by the criteria described previously herein, is sacrificed. The cells and/or tissues of the mouse are then examined at the cellular level and/or at the molecular level and compared to the cells and/or tissues from transgene-negative littermates.

Alternatively, the cells and/or tissues from a transgenic mouse of the present invention that is a suitable model for heart failure are compared to the cells and/or tissues from a transgenic mouse of the present invention that is not a suitable model for congestive heart failure (e.g., a female transgenic mouse). Examples of experiments that can be performed to compare the cells and/or tissues of the mice include, but are not limited to, morphological examination of cardiac cells; histological examination of coronary vessels, of heart sections, of myocytes and/or of myofibrils; evaluation of cardiac myocyte DNA replication and/or expression; assays to evaluate enzyme activity; and assays studying programmed cell death, or apoptosis. The methods to perform such experiments are standard and are well known in the art. Many of these experiments are described in detail in the Examples section herein.

Another embodiment of the present invention relates to a system in which to test drug candidates for prevention or treatment of congestive heart failure. In this embodiment, a transgenic mouse which is a model for congestive heart failure serves as an in vivo system to evaluate the effect of drug candidates for prevention or treatment of congestive heart failure. Specifically, a transgenic mouse of the present invention which meets the criteria for a model of congestive heart failure as described herein is administered a candidate compound to be evaluated. The mouse is then evaluated for physiological and pathological changes which indicate the efficacy of the compound for prevention or treatment of congestive heart failure. The mouse is compared to a transgenic mouse that meets the criteria for congestive heart failure that did not receive the compound. As for the method above, a transgene-negative littermate or a female transgenic mouse can also serve as a control or point of comparison. A drug or compound to be evaluated refers to any chemical compound that can be administered to an animal as an aid in the diagnosis, treatment or prevention of disease or an abnormal condition.

In accordance with the present invention, acceptable protocols to administer a candidate drug or compound include the mode of administration and the effective amount of candidate drug or compound administered to an animal, including individual dose size, number of doses and frequency of dose administration. Determination of such protocols can be accomplished by those skilled in the art. Suitable modes of administration can include, but are not limited to, oral, nasal, topical, transdermal, rectal, and parenteral routes. Preferred parenteral routes can include, but are not limited to, subcutaneous, intradermal, intravenous, intramuscular and intraperitoneal routes. Preferred topical routes include inhalation by aerosol (i.e., spraying) or topical surface administration to the skin of an animal.

According to the method of the present invention, an effective amount of a candidate drug or compound to administer to an animal comprises an amount that is capable of preventing or treating congestive heart failure, without being toxic to the animal. An amount that is toxic to an animal comprises any amount that causes damage to the structure or function of an animal (i.e., poisonous). Prevention or treatment of congestive heart failure can be assessed as a change (i.e., increase or reduction) in a phenotypic characteristic associated with congestive heart failure, such change being effective to prevent or treat congestive heart failure.

Yet another embodiment of the present invention relates to the use of a transgenic mouse having phenotypic characteristics of congestive heart failure to study the effects of external factors on congestive heart failure. Such factors include, but are not limited to, diet and exercise. In this embodiment, a first transgenic mouse which meets the criteria of a model for congestive heart failure as described herein is fed a particular diet or submitted to a particular exercise regimen which is to be established as a normal, or control, regimen. For example, a normal, or control diet can be the diet that is fed to wild type mice of the particular transgenic background (e.g., C57Bl/6) as established for a normal animal facility. Non-transgenic littermates and/or female transgenic mice can be used as additional controls. This regimen is then modulated to study the effect of such a modulated external factor on heart failure. Again, the same controls can be used. The second transgenic mouse is then monitored for a change in one or more characteristics of congestive heart failure in comparison to the first transgenic mouse (having a normal regimen) and to the transgene-negative littermates or female transgenic mice. For example, the effects of a low-fat diet or of moderate exercise on the development of characteristics associated with congestive heart failure can be evaluated using the transgenic mouse model for congestive heart failure of the present invention.

Another embodiment of the present invention relates to the use of a transgenic mouse which meets the criteria for a model for congestive heart failure of the present invention to study specific conditions or diseases associated with congestive heart failure. Such a method includes the steps of (a) harvesting cells and tissues from a transgenic mouse of the present invention and comparing the cells and tissues to a transgene-negative littermate to evaluate a biochemical, physiological, and/or molecular event related to a disease or condition associated with congestive heart failure. Alternatively, a transgenic mouse of the present invention can be administered a compound to be tested for its affect on a disease or condition associated with congestive heart failure, such mouse being compared to a transgenic mouse that did not receive the compound. Such specific conditions or diseases associated with congestive heart failure include, but are not limited to dilated cardiomyopathy, hypertrophic cardiomyopathy, acute aortic regurgitation, tricuspid stenosis, constrictive pericarditis, acute infective endocarditis, ischemia heart disease, hypertension, primary myocardial disease, valvular disease, pericardial disease, hyperthyroidism, anemia, arteriovenous fistula, beriberi and Paget's disease.

Yet another embodiment of the present invention relates to a method to study heart failure by breeding a transgenic mouse of the present invention which meets the criteria of a model for congestive heart failure with other genetically altered mice. Examples of other genetically altered mice which would be candidates for such breeding experiments include mice with manipulations in systems such as the renin-angiotensin system, the β adrenergic receptor pathway, and calcium handling systems. See, for example, Milano et al., *Science,* 264, 582–586 (1994); Gaudin et al., *J. Clin. Invest.,* 95, 1676–1683 (1995); Iwase et al., *Circ. Res.,* 78, 517–524 (1996); Bertin et al., *Cardiovasc. Res.,* 27, 1606–1612 (1993); Koch et al., *Science,* 268, 1350–53 (1995); Samama et al., *Proc. Natl. Acad. Sci. USA,* 94, 137–141 (1997); Milano et al., *Proc. Natl. Acad. Sci. USA,* 91, 10109–10113 (1994). In one embodiment of this method, the second transgenic mouse has incorporated into its genome a transgene comprising a nucleic acid sequence encoding a $\beta_1$-adrenergic receptor.

Bertin et al. have described a transgenic mouse overexpressing human $\beta_1$ adrenergic receptor. Bertin et al., *Cardiovasc. Res.,* 27, 1606–1612 (1993); PCT application WO 94/04668. Receptor overexpression was targeted exclusively to the atria by using the human atrial natriuretic factor promoter. Similarly, Milano et al. have described the creation of a transgenic mouse overexpressing the human β₂ adrenergic receptor using a murine β-myosin heavy chain (αMHC) promoter. Milano et al., *Science*, 264, 582–586 (1994); Milano et al., *J. Thoracic Cardiovasc. Surg.*, 109, 236–241 (1995). The use of this promoter targeted gene expression to the myocardium, both in the atria and ventricles. Either of these mice could be candidates for breeding with a transgenic mouse of the present invention.

Alternatively, a transgenic mouse of the present invention can be produced which carries one or more additional transgenes in addition to the mutated α myosin heavy chain transgene of the present invention.

This embodiment can also be used to study a condition or disease associated with congestive heart failure. For example, a mouse which has been genetically modified to be a model for a particular condition or disease associated with congestive heart failure can be bred with a transgenic mouse of the present invention to produce a mouse useful for studying the correlation between the particular condition or disease and congestive heart failure. Such specific conditions or diseases associated with congestive heart failure include, but are not limited to dilated cardiomyopathy, hypertrophic cardiomyopathy, acute aortic regurgitation, tricuspid stenosis, constrictive pericarditis, acute infective endocarditis, ischemia heart disease, hypertension, primary myocardial disease, valvular disease, pericardial disease, hyperthyroidism, anemia, arteriovenous fistula, beriberi and Paget's disease.

Another embodiment of the present invention relates to a method to produce a transgenic mouse which is a model for studying heart failure. Such a method includes the steps of: (a) introducing into an embryonic cell of a mouse a transgene comprising: (1) a heart tissue-specific promoter; and, (2) a nucleic acid sequence encoding an amino acid sequence of an α myosin heavy chain protein. The nucleic acid sequence has a first mutation comprising a point mutation which results in an Arg403Gln mutation in the amino acid sequence and a second mutation comprising an interstitial deletion in a portion of the nucleic acid sequence that encodes an actin binding domain; and, (b) obtaining progeny having the transgene stably incorporated into the genome. The transgene is expressed in the heart tissues of the progeny. In one embodiment, the method includes the further step (c) of selecting males from the progeny that have the transgene stably incorporated into the genome. The method can further include selecting male progeny of at least about 5 months of age. As discussed above, female transgenic mice can also be selected as a model for studying heart failure, because environmental and gender-biased contributions to the disease can be studied using female transgenic mice.

Yet another embodiment of the present invention relates to a transgenic mouse that is a model for hypertrophic cardiomyopathy. Such a transgenic mouse has incorporated into its genome a transgene comprising: (a) a heart tissue-specific promoter; and, (b) a nucleic acid sequence encoding an amino acid sequence of a α myosin heavy chain protein. The nucleic acid sequence has a first mutation comprising a point mutation which results in an Arg403Gln mutation in the amino acid sequence, and a second mutation comprising an interstitial deletion in a portion of the nucleic acid sequence that encodes an actin binding domain. The transgene is expressed in the heart tissues of the transgenic mouse at a level sufficient to promote hypertrophic cardiomyopathy in the mouse. Such a mouse has been described in detail previously herein. In particular, a transgenic mouse of the present invention that is a suitable model for hypertrophic cardiomyopathy include any female transgenic mouse of the present invention and young, male transgenic mice of the present invention. Preferably, male transgenic mice of the present invention that are suitable models for hypertrophic cardiomyopathy are less than about 8 months of age, preferably less than about 7 months of age, more preferably less than about 6 months of age, and most preferably, less than about 5 months of age. Preferably, the transgene is expressed at least at the minimum levels disclosed herein for mice that can be a model for congestive heart failure.

The following examples are provided for the purposes of illustration and are not intended to limit the scope of the present invention.

EXAMPLES

Example 1

The following example illustrates the production of transgenic mice of the present invention.

Five transgenic mouse lines with cardiac-specific expression of a mutant α myosin heavy chain were created. In contrast to humans, where β myosin heavy chain is the predominant cardiac myosin isoform, α myosin heavy chain is the predominant isoform of the adult mouse ventricle. Therefore, a mutant rat α myosin heavy chain cDNA was used to construct the transgene coding region. Rat and mouse α myosin heavy chain are 98.9% identical at the amino acid level (22 differences out of 1938 amino acids) with the differences being similar to the neutral polymorphisms found between various inbred mouse strains. None of the seven nonconservative differences between rat and mouse α myosin heavy chain are found in the head or subfragment 1 (S1) region of the myosin heavy chain, the site of most HCM mutations. The differences are found only in the subfragment 2 (S2; two amino acids) or light meromyosin (LMM; five amino acids) regions. In addition, no HCM mutations have been identified in amino acids that differ between rat and mouse α myosin heavy chain.

The transgene which is schematically illustrated in FIG. 1, was constructed using standard cloning techniques. The transgene coding region consists of a rat α myosin heavy chain cDNA containing two mutations: (a) a point mutation at position 1445 of a G to an A (G1445A), which results in an amino acid substitution at amino acid position 403 from an arginine to a glutamine (Arg403Gln); and, (b) a deletion of amino acids 468–527 in the putative actin binding domain, bridged by the addition of 8 nonmyosin amino acids (SerSerLeuProHisLeuLysLeu). The combination of these two mutations was predicted by the present inventors to produce a very strong dominant negative effect by altering the interaction of myosin with actin. In addition, the deletion mutation allowed the transgene protein to be distinguished electrophoretically from the endogenous mouse myosin heavy chain. The coding region of the transgene was flanked by a hybrid intron derived from the mammalian expression construct pMT21 at the 5' end (Genetics Institute, Cambridge Mass.) and the SV40 small t intron at the 3' end. Transgene expression was driven by approximately 3.3 kb of rat α myosin heavy chain 5' flanking DNA (obtained from B. Markham, Medical College of Wisconsin), and polyadenylation sequences were provided by SV40 small t DNA.

Transgene sequences were excised from the prokaryotic vector sequences, purified on agarose gels, and then injected into the pronuclei of fertilized mouse eggs from CBA X C57Bl/6 (F1 cross) mice according to standard techniques. Founder animals were identified by Southern blotting and bred to C57Bl/6 mice.

Five independent transgenic lines were established (lines 131, 136, 138, 140, and 143) and cardiac-specific expressions of the transgene mRNA was confirmed by ribonuclease (RNase) protection analysis as follows (data not shown). RNA was purified using the guanidinium-acid phenol method. An antisense riboprobe was generated from the 5' end of the transgene using the Promega Riboprobe kit (Promega, Madison, Wis., U.S.A.) and purified by guanidinium-acid phenol extraction followed by isopropanol precipitation. The probe hybridizes to approximately 300 and 200 bp protected fragments for the transgene and the endogenous mouse myosin heavy chain mRNAs, respectively. A five hundred thousand-counts per minute probe was combined with 3 µg of RNA and hybridized overnight at 55° C. in 86% formamide, 2 mM EDTA, 0.433 M NaCl, 43 mM Pipes, pH 6.9. Samples were digested at 37° C. for 1.5 hours with 40 units of TI RNAase (Boehringer Mannheim, Indianapolis, Ind., U.S.A.) and 0.5 µg of RNAase A (Boehringer Mannheim) in 0.5 ml of 0.3 M NaCl, 30 mM Tris-HCl, pH 7.5, 50 µg/ml yeast tRNA. Digestion was stopped by the sequential addition of 10 µl 20% SDS and 50 µl stop buffer (4 M ammonium acetate, 100 mM EDTA, 1 mg/ml yeast tRNA). The samples were phenol:chloroform-extracted, ethanol-precipitated, and then electrophoresed on a 5% acrylamide gel under denaturing conditions. Long exposures revealed very low levels of the endogenous mouse α myosin heavy chain in the lung, however, transgene expression was detected only in the heart. Transgene message was abundant in the hearts of these mice and was found at 26–50% of the endogenous mouse myosin heavy chain levels (not shown).

Example 2

The following example shows that the transgenic mice of the present invention are a model for familial hypertrophic cardiomyopathy (HCM).

If the transgenic mice of the present invention are to function as a model for HCM, they should exhibit several phenotypic features found in most individuals with the disease. These include myocyte hypertrophy, myocellular disarray, interstitial fibrosis, and small vessel coronary disease. Hearts from each transgenic line were examined at 12–14 weeks of age for evidence of these features. Briefly, paraffin sections of hearts from control and transgenic mice were stained with Masson's trichrome or hemotoxylin/eosin. In all cases the atria were normal but significant cardiac histopathology was evident in the left ventricle. In a few animals, some abnormal myocytes were seen in the right ventricle but the vast majority of hypertrophied cells were found in the left ventricle. Foci of myocellular disarray were found throughout the left ventricle accompanied by evidence of increased matrix accumulation. Hearts from 5 month old 140 line transgenic mice were embedded in plastic resin and abnormal regions within the left ventricle were identified in thick sections of plastic embedded tissue. Thin sections were cut from these regions, stained with uranyl acetate and lead citrate and examined on the electron microscope. Myofibrillar disarray as well as degeneration were evident. When areas with myocellular disarray were identified and then examined at the electron microscope level, several abnormalities were seen. Degenerating myofibrils, prominent collagen deposits and z-line streaming were apparent. It is interesting to note that severely damaged myocytes often were adjacent to apparently normal cells. In these instances, intact myofibrils were absent near the intercalated discs, implying a lack of force transmission between the adjacent myocytes. The electron micrographs of the myocellular disarray (not shown herein) are virtually indistinguishable from published micrographs of skeletal muscle biopsies from HCM human patients.

Small vessel coronary disease, seen histopathologically as thickening of the medial and intimal layer of small coronary vessels, is found in many patients with HCM and is also present in feline and porcine HCM. Abnormal coronary vessels were found in the hearts of all transgenic mouse lines. Not all vessels were hypertrophied, as evidenced by the presence of normal and abnormal vessels within the same animal. Such vessel-to-vessel heterogeneity is also seen in humans. Mutant α myosin heavy chain expression was not detected in smooth muscle rich tissues such as uterus, suggesting that it also is not expressed in the smooth muscle layer of the coronary arteries. The smooth muscle hypertrophy seen in small coronary arteries is most likely the result of a compensatory response of the vasculature to dysfunctional cardiac myocytes. While all five lines of mice exhibited histopathology characteristic of HCM, two were relatively mild and three were quite strong in phenotype at the microscopic level. Two transgenic lines (lines 131 and 140) were selected as examples of mild and strong phenotypes, respectively, and retained for further study.

Actin and myosin are normally found in a precise ratio in muscle and alterations in this stoichiometry could have profound effects. To determine whether expression of the mutant myosin heavy chain perturbed contractile protein stoichiometry in these transgenic mice, cardiac myofibrils were prepared from transgenic mice (131 and 140 lines). The ratio of myosin to actin in these preparations was determined by densitometry and compared with control mouse cardiac myofibrils (not shown). The myosin/actin ratios were found to be identical, although very small alterations undetectable by the present analysis cannot be ruled out.

The amount of transgene protein in heart homogenates from control, 131 line, and 140 line mice was determined by SDS-acrylamide gel electrophoresis followed by immunoblotting and densitometry as follows. Heart homogenates or myofibrils were electrophoretically separated on 6% SDS-polyacrylamide gels according to Laemmli. Electrophoresis was continued until the myosin heavy chains had migrated approximately 8 cm through a 11 cm separating gel. Immunoblotting was performed using an anti-α myosin heavy chain monoclonal antibody, BAG5 (obtained from Dr. S. Schiaffino, Padova, Italy), and chemiluminescent images were quantified using a Molecular Dynamics laser densitometer.

Acrylamide gels were run which optimized the size differences between the mutant and endogenous wild type species. Results showed that the mutant protein comprises 10–12% of the total myosin in Line 140 and 0.6–2.5% in Line 131. Identical results were obtained whether heart homogenates or purified myofibrils were examined. The low levels of mutant protein, in conjunction with the apparently normal actin/myosin stoichiometry, suggest that the severe phenotype is due to the dominant effect of the mutant such that a relatively small number of mutant polypeptides exert a "drag" on sarcomere function. Consistent with this conclusion are findings that a mixture of mutant (Arg403Gln) and wild-type myosin proteins exhibits the properties of the mutant unless the wild-type constitutes greater than 60% of the mixture.

Figure 2:
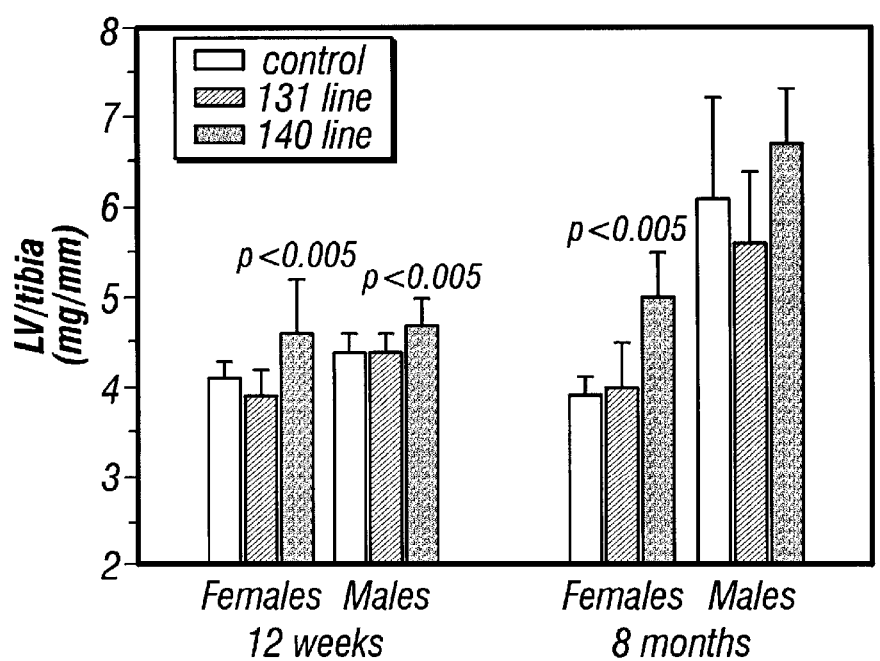
FIG. 2 is a graph illustrating left ventricle weights for aged matched transgenic male and female mice and their negative littermates.

Atria, left ventricle and right ventricle weights were determined in age-matched transgenic mice (12 weeks and 8 months of age) with negative littermates serving as controls (Table 1 and FIG. 2). Table 1 shows that at 12 weeks of age, the 140 line exhibited significant increases in left and right ventricular mass compared with controls (females: left a ventricle (LV) 12% increase, and right ventricle (RV) 14% increase; males: LV 7% increase and RV 9% increase) while no difference in body weight or tibial length was seen. Data in Table 1 were analyzed using an unpaired Student's t test. p values are indicated in the table. The cardiac hypertrophy in these animals is accompanied by increased message levels of atrial natriuretic factor (ANF) and α-skeleton actin, two molecular markers of cardiac hypertrophy. Animals from the 131 line did not exhibit significant cardiac hypertrophy at this age. Although large numbers of animals from the other three lines of mice were not examined for heart mass measurements, every transgenic heart from those three lines was hypertrophic by 12 weeks of age. Although the 131 line did exhibit increased levels of ANF and α-skeletal actin mRNAs, the levels of these molecular markers of hypertrophy were significantly less than in the 140 line.

esis at a cellular and molecular level will provide information helpful for addressing this question. The present inventors have created five independent transgenic mouse lines with cardiac-specific expression of a mutant myosin heavy chain. Like human HCM, the animal model shows left ventricular hypertrophy, myocyte hypertrophy, myocellular disarray, fibrosis, and small vessel coronary disease. Based on these findings, the transgenic mice of the present invention are a good model for HCM and their analysis provides insight into the mechanisms involved in developing the disease phenotype.

It is clear that mutant contractile proteins are the initial result in the development of HCM, but patients do not die purely as the result of sarcomeric dysfunction. Without being bound by theory, the present inventors believe that mutations in β myosin heavy chain, cardiac troponin T, α-tropomyosin, and cardiac myosin binding protein C trigger a pathogenic pathway resulting in a common phenotype, hypertrophic cardiomyopathy. The present analysis of murine HCM suggests that the appearance of histologic

TABLE 1

Cardiac hypertrophy in transgenic mice

|   | Heart (mg) | Atria (mg) | RV (mg) | LV (mg) | Body (g) | Tibial Length (mm) |
|---|---|---|---|---|---|---|
| A. Heart and Chamber Weights, Female Mice | | | | | | |
| Control (n = 16) | 99.6 ± 4.4 | 5.2 ± 0.6 | 19.1 ± 1.4 | 68.8 ± 3.7 | 22.2 ± 1.3 | 16.9 ± 0.2 |
| 131 line (n = 8) | 94.3 ± 5.8[a] | 4.3 ± 1.0[a] | 18.5 ± 1.0[a] | 65.0 ± 5.3[a] | 21.1 ± 1.0[a] | 16.8 ± 0.3 |
| 140 line (n = 9) 12 weeks | 114.4 ± 12.4[a] | 5.2 ± 1.0 | 21.8 ± 2.1[b] | 76.9 ± 8.7[b] | 22.0 ± 3.0 | 16.7 ± 0.4 |
| 8 months | | | | | | |
| Control (n = 8) | 96.6 ± 2.9 | 4.5 ± 0.7 | 17.5 ± 1.3 | 66.8 ± 3.9 | 22.6 ± 2.1 | 17.3 ± 0.4 |
| 131 line (n = 10) | 104.4 *10.9[a] | 4.8 ± 1.1 | 17.6 ± 2.0 | 73.0 ± 8.7 | 24.9 ± 2.7 | 18.1 ± 0.8[a] |
| 140 line (n = 16) | 125.8 ± 14.9[b] | 5.2 ± 1.0 | 23.3 ± 3.5[b] | 88.4 ± 9.8[b] | 28.0 ± 3.0[b] | 17.7 ± 0.4[a] |
| B. Heart and Chamber Weights, Male Mice 12 weeks | | | | | | |
| Control (n = 13) | 111.0 ± 55 | 5.8 ± 0.6 | 22.1 ± 1.6 | 74.7 ± 4.2 | 26.2 ± 1.0 | 17.2 ± 0.3 |
| 131 line (n = 9) | 109.5 ± 5.7 | 5.0 ± 0.8[a] | 21.8 ± 2.3 | 74.1 ± 3.2 | 25.6 ± 1.9 | 16.9 ± 0.2 |
| 140 line (n = 7) | 119.0 ± 6.7[a] | 5.9 ± 1.3 | 24.1 ± 1.8[a] | 79.8 ± 4.6[a] | 25.6 ± 1.5 | 17.0 ± 0.2 |
| 8 months | | | | | | |
| Control (n = 7) | 153.8 ± 26.9 | 7.6 ± 2.6 | 27.4 ± 5.9 | 107.3 ± 19.0 | 33.2 ± 4.9 | 17.8 ± 0.3 |
| 131 line (n = 8) | 138.1 ± 16.8 | 6.4 ± 1.0 | 24.5 ± 3.6 | 98.6 ± 14.0 | 31.2 ± 3.8 | 17.7 ± 0.2 |
| 140 line (n = 7) | 161.4 ± 15.4 | 7.2 ± 2.1 | 27.4 ± 3.3 | 116.0 ± 11.9 | 33.5 ± 3.9 | 17.5 ± 0.3 |

[a]Values = SD.
[b]p<005.
[c]<0.005.

Molecular genetic analysis has revealed that hypertrophic cardiomyopathy is often associated with mutations in genes encoding contractile proteins. This has led to the hypothesis that HCM is a disease of the sarcomere. However, the exact relationship between mutant contractile proteins and the phenotype remains unclear. Characterizing HCM pathogenabnormalities may be one of the "triggering" events in the development of HCM. Mice from both the 131 and 140 lines exhibit cardiac histopathology, while increased cardiac mass is seen only in the 140 line, suggesting that the appearance of histologic abnormalities precedes the development of hypertrophy. Similar examples of HCM without chamber hypertrophy have been reported in the patient population. The ultrastructural abnormalities seen in these transgenic mice suggest a possible mechanism for the triggering event. The degeneration of myofibrils at the site of their attachment to the intercalated disk would result in a myocyte unable to transmit force to its neighbor. This "gap" in the force-producing machinery could then trigger compensatory responses in the tissue, such as reorientation of the surrounding myocytes (disarray) and hypertrophy. Thus, expression of low levels of a strongly dominant negative mutant protein (such as seen in the present transgenic mice) could trigger profound effects in the heart.

Without being bound by theory, the present inventors believe that there exists a threshold of sarcomeric dysfunction which, when surpassed, triggers a greater hypertrophic response. The nature of the mutant protein, the work load imposed upon the muscle as well as the amount of the mutant protein may all determine when this threshold is reached. Thus, individuals with two copies of a fairly benign mutation would be predicted to exhibit a more severe phenotype than family members with only one copy of the mutant gene, as has been reported. In addition, mouse lines with greater (140 line) or lesser (131 line) expression of a mutant myosin heavy chain would be predicted to exhibit stronger or milder phenotypes, respectively, as shown by the data herein.

Example 3

The following example demonstrates that older male transgenic mice of the present invention are models for congestive heart failure.

As described above in Example 2, left ventricle weights were determined for age-matched transgenic mice and their negative littermates and normalized to tibial lengths. By 8 months of age the degree of left ventricular hypertrophy seen in females from the 140 line had more than doubled to 32%. These changes were apparent in the absolute weight of the left ventricles (12–32%) or in ventricular weights normalized to tibial length (12–28%). In contrast, at 8 months of age the mean heart weight of 140 line males, while still slightly larger than controls, had lost all statistical significance (p>0.1). There is extreme variability in heart and body sizes seen in older male mice (both control and transgenic). However, gross examination of formaldehyde-fixed hearts indicated that the 140 line hearts had overall dimensions that were much greater than the controls (data not shown).

Formaldehyde-fixed hearts, both control and 140 line transgenic, were bisected axially by an incision through the anterior face of the left ventricle. The two halves of the heart were splayed open to reveal the left ventricular cavity. In this position, the atria are hidden behind the two halves of the heart, the left ventricular free wall is distal and the right ventricular free wall is medial to the ventricle axis. This group (i.e., older male mice from the 140 line) exhibited significant chamber dilation. In control hearts the left ventricular cavity was a normal crescent shape (seven out of seven hearts examined) while in all 8-month 140 line males (five hearts examined) the left ventricular cavity was dilated and almond-shaped.

In summary, in the 140 line older male and female mice exhibit distinct phenotypes. While the cardiac hypertrophy was increased in older female animals, male 140 line mice exhibited significant dilation of the left ventricle. Although sex-specific differences in the HCM phenotype have not been reported in humans, clinical heterogeneity is a hallmark of this disease. In addition, HCM patients often exhibit progressive wall thinning or relative ventricular dilation as they age, indicating congestive heart failure. The development of ventricular dilation resulting in end-stage heart failure (i.e., congestive heart failure) has also been reported in families where the primary end result of the disease is cardiac sudden death. The development of sex-specific phenotypes in the 140 line animals provides a fortuitous tool for deciphering the factors contributing to the clinical course of congestive heart failure as well as the molecular mechanisms leading to dilated cardiomyopathy.

Example 4

The following example shows that the transgenic mouse of the present invention is a model of hypertrophic cardiomyopathy, and that older, male transgenic mice of the present invention are models for congestive heart failure, exhibiting dilation, wall thinning and systolic dysfunction.

Transgenic mice of the present invention, which exhibit features of human HCM including myocyte hypertrophy, myocellular disarray, abnormal small intramural coronary arteries and significant LVH, were tested over time using echocardiography. By 3 months of age, both male and female transgenic mice had significant septal hypertrophy (IVS=1.19 mm vs 0.85 mm in controls) with preserved systolic function (%FS=54 vs 53) and chamber dimensions (LVEDD=2.48 mm vs 2.66 mm). At 10–12 months, females showed progressive hypertrophy and normal %FS. 10–12 month old males, however, have developed chamber dilation (LVEDD=3.48 mm), loss of hypertrophy (IVS=0.92 mm) and decreased systolic function (%FS=36). In summary, a genetic mouse model developed to study hypertrophic cardiomyopathy exhibits an unexpected gender specific difference in phenotypic expression of symptoms of congestive heart failure with age. This course parallels the course of hypertrophy leading to congestive heart failure in elderly humans with aortic stenosis, as documented by serial echocardiography.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 8 amino acids
      (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO:1:

Ser Ser Leu Pro His Leu Lys Leu
1               5

(2) INFORMATION FOR SEQ ID NO:2:

(i) SEQUENCE CHARACTERISTICS:
        (A) LENGTH: 5661 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..5661

(xi) SEQUENCE DESCRIPTION: SEQ ID NO:2:

ATG ACG GAT GCC CAG ATG GCT GAC TTC GGG GCG GCA CGA TAC CTC CGC       48
Met Thr Asp Ala Gln Met Ala Asp Phe Gly Ala Ala Arg Tyr Leu Arg
 1               5                  10                  15

AAG TCA GAG AAG GAG CGC CTA GAG GCC CAG ACC CGG CCC TTT GAC ATC       96
Lys Ser Glu Lys Glu Arg Leu Glu Ala Gln Thr Arg Pro Phe Asp Ile
                20                  25                  30

CGC ACA GAG TGC TTC GTG CCT GAT GAC AAG GAG GAG TAT GTC AAG GCC      144
Arg Thr Glu Cys Phe Val Pro Asp Asp Lys Glu Glu Tyr Val Lys Ala
            35                  40                  45

AAG ATC GTG TCC CGG GAA GGG GGC AAG GTC ACT GCC GAA ACT GAA AAC      192
Lys Ile Val Ser Arg Glu Gly Gly Lys Val Thr Ala Glu Thr Glu Asn
        50                  55                  60

GGC AAG ACG GTG ACT GTG AAG GAG GAC CAG GTG ATG CAG CAG AAC CCT      240
Gly Lys Thr Val Thr Val Lys Glu Asp Gln Val Met Gln Gln Asn Pro
 65                  70                  75                  80

CCG AAA TTC GAC AAG ATC GAG GAC ATG GCC ATG CTG ACC TTC CTG CAT      288
Pro Lys Phe Asp Lys Ile Glu Asp Met Ala Met Leu Thr Phe Leu His
                 85                  90                  95

GAG CCA GCT GTG CTC TAC AAT CTC AAG GAG CGC TAT GCG GCC TGG ATG      336
Glu Pro Ala Val Leu Tyr Asn Leu Lys Glu Arg Tyr Ala Ala Trp Met
            100                 105                 110

ATC TAT ACC TAC TCA GGC CTC TTC TGT GTC ACC GTC AAC CCC TAT AAG      384
Ile Tyr Thr Tyr Ser Gly Leu Phe Cys Val Thr Val Asn Pro Tyr Lys
        115                 120                 125

TGG CTG CCA GTG TAC AAT GCG GAA GTG GTA GCT GCC TAC CGG GGC AAG      432
Trp Leu Pro Val Tyr Asn Ala Glu Val Val Ala Ala Tyr Arg Gly Lys
130                 135                 140

AAG AGG AGC GAG GCT CCA CCC CAC ATC TTC TCC ATC TCT GAC AAC GCC      480
Lys Arg Ser Glu Ala Pro Pro His Ile Phe Ser Ile Ser Asp Asn Ala
145                 150                 155                 160

TAT CAG TAC ATG CTG ACA GAT CGG GAG AAC CAG TCC ATC CTC ATC ACT      528
Tyr Gln Tyr Met Leu Thr Asp Arg Glu Asn Gln Ser Ile Leu Ile Thr
                165                 170                 175

GGA GAA TCC GGA GCG GGG AAG ACT GTC AAC ACG AAG CGT GTC ATC CAG      576
Gly Glu Ser Gly Ala Gly Lys Thr Val Asn Thr Lys Arg Val Ile Gln
            180                 185                 190

TAC TTT GCT AGC ATT GCA GCC ATA GGG GAC CGT AGC AAG AAG GAC AAT      624
Tyr Phe Ala Ser Ile Ala Ala Ile Gly Asp Arg Ser Lys Lys Asp Asn
        195                 200                 205
```

```
CCT AAT GCA AAC AAG GGC ACC CTG GAG GAC CAG ATT ATC CAG GCT AAC        672
Pro Asn Ala Asn Lys Gly Thr Leu Glu Asp Gln Ile Ile Gln Ala Asn
    210                 215                 220

CCT GCT CTG GAG GCC TTT GGC AAC GCC AAG ACT GTC CGG AAT GAC AAC        720
Pro Ala Leu Glu Ala Phe Gly Asn Ala Lys Thr Val Arg Asn Asp Asn
225                 230                 235                 240

TCC TCC CGC TTT GGG AAG TTC ATC AGG ATC CAC TTT GGA GCC ACA GGA        768
Ser Ser Arg Phe Gly Lys Phe Ile Arg Ile His Phe Gly Ala Thr Gly
                245                 250                 255

AAG CTG GCT TCT GCA GAC ATA GAG ACC TAC CTT CTG GAG AAG TCC CGG        816
Lys Leu Ala Ser Ala Asp Ile Glu Thr Tyr Leu Leu Glu Lys Ser Arg
            260                 265                 270

GTG ATC TTC CAG CTA AAG GCT GAG AGG AAC TAC CAT ATC TTC TAC CAG        864
Val Ile Phe Gln Leu Lys Ala Glu Arg Asn Tyr His Ile Phe Tyr Gln
        275                 280                 285

ATC CTG TCC AAC AAG AAG CCG GAG CTG CTG GAC ATG CTG CTG GTT ACC        912
Ile Leu Ser Asn Lys Lys Pro Glu Leu Leu Asp Met Leu Leu Val Thr
    290                 295                 300

AAC AAC CCG TAC GAC TAT GCC TTC GTC TCT CAG GGA GAG GTG TCT GTG        960
Asn Asn Pro Tyr Asp Tyr Ala Phe Val Ser Gln Gly Glu Val Ser Val
305                 310                 315                 320

GCC TCC ATT GAT GAC TCC GAG GAG CTT TTG GCC ACT GAT AGC GCC TTT       1008
Ala Ser Ile Asp Asp Ser Glu Glu Leu Leu Ala Thr Asp Ser Ala Phe
                325                 330                 335

GAT GTG CTG GGC TTC ACA GCA GAG GAG AAG GCC GGT GTC TAC AAG CTG       1056
Asp Val Leu Gly Phe Thr Ala Glu Glu Lys Ala Gly Val Tyr Lys Leu
            340                 345                 350

ACA GGC GCC ATC ATG CAC TAT GGG AAC ATG AAG TTC AAG CAG AAG CAG       1104
Thr Gly Ala Ile Met His Tyr Gly Asn Met Lys Phe Lys Gln Lys Gln
        355                 360                 365

CGG GAG GAG CAG GCG GAG CCA GAC GGC ACA GAA GAT GCT GAC AAA TCT       1152
Arg Glu Glu Gln Ala Glu Pro Asp Gly Thr Glu Asp Ala Asp Lys Ser
    370                 375                 380

GCC TAC CTC ATG GGG CTG AAC TCA GCC GAC CTG CTC AAG GGT CTG TGT       1200
Ala Tyr Leu Met Gly Leu Asn Ser Ala Asp Leu Leu Lys Gly Leu Cys
385                 390                 395                 400

CAC CCT CAG GTG AAG GTG GGT AAC GAG TAT GTC ACC AAG GGG CAG AGT       1248
His Pro Gln Val Lys Val Gly Asn Glu Tyr Val Thr Lys Gly Gln Ser
                405                 410                 415

GTA CAG CAG GTG TAC TAT TCC ATC GGG GCA CTG GCC AAG TCA GTG TAC       1296
Val Gln Gln Val Tyr Tyr Ser Ile Gly Ala Leu Ala Lys Ser Val Tyr
            420                 425                 430

GAG AAG ATG TTC AAC TGG ATG GTG ACA CGC ATC AAC GCA ACC CTG GAG       1344
Glu Lys Met Phe Asn Trp Met Val Thr Arg Ile Asn Ala Thr Leu Glu
        435                 440                 445

ACC AAG CAG CCA CGC CAG TAC TTC ATA GGT GTC CTG GAC ATC GCC GGC       1392
Thr Lys Gln Pro Arg Gln Tyr Phe Ile Gly Val Leu Asp Ile Ala Gly
    450                 455                 460

TTT GAG ATC TCA AGC CTG CCA CAC CTC AAG CTC ATG GGC ATC ATG TCC       1440
Phe Glu Ile Ser Ser Leu Pro His Leu Lys Leu Met Gly Ile Met Ser
465                 470                 475                 480

ATC CTG GAG GAG GAG TGC ATG TTC CCC AAG GCC ACA GAC ATG ACC TTC       1488
Ile Leu Glu Glu Glu Cys Met Phe Pro Lys Ala Thr Asp Met Thr Phe
                485                 490                 495

AAG GCC AAG CTG TAC GAC AAC CAC CTG GGC AAG TCC AAC AAC TTC CAG       1536
Lys Ala Lys Leu Tyr Asp Asn His Leu Gly Lys Ser Asn Asn Phe Gln
            500                 505                 510

AAG CCT CGC AAT GTC AAG GGG AAG CAG GAA GCC CAC TTC TCT CTG GTC       1584
Lys Pro Arg Asn Val Lys Gly Lys Gln Glu Ala His Phe Ser Leu Val
        515                 520                 525
```

```
CAC TAT GCT GGC ACC GTG GAC TAC AAC ATC TTG GGC TGG CTG GAG AAG      1632
His Tyr Ala Gly Thr Val Asp Tyr Asn Ile Leu Gly Trp Leu Glu Lys
        530                 535                 540

AAC AAG GAC CCT CTC AAC GAG ACG GTG GTG GGG CTG TAC CAG AAG TCC      1680
Asn Lys Asp Pro Leu Asn Glu Thr Val Val Gly Leu Tyr Gln Lys Ser
545                 550                 555                 560

TCC CTC AAA CTC ATG GCC ACA CTC TTC TCC ACC TAT GCT TCT GCT GAT      1728
Ser Leu Lys Leu Met Ala Thr Leu Phe Ser Thr Tyr Ala Ser Ala Asp
                565                 570                 575

ACC GGT GAC AGT GGG AAA GGC AAA GGA GGC AAG AAG AAA GGC TCA TCC      1776
Thr Gly Asp Ser Gly Lys Gly Lys Gly Gly Lys Lys Lys Gly Ser Ser
            580                 585                 590

TTC CAG ACA GTG TCT GCT CTC CAC CGG GAA AAT CTG AAC AAG CTG ATG      1824
Phe Gln Thr Val Ser Ala Leu His Arg Glu Asn Leu Asn Lys Leu Met
        595                 600                 605

ACA AAC CTG AGG ACC ACC CAT CCT CAC TTT GTG CGC TGC ATC ATC CCC      1872
Thr Asn Leu Arg Thr Thr His Pro His Phe Val Arg Cys Ile Ile Pro
610                 615                 620

AAT GAG CGG AAG GCT CCA GGG GTG ATG GAC AAC CCC CTG GTC ATG CAC      1920
Asn Glu Arg Lys Ala Pro Gly Val Met Asp Asn Pro Leu Val Met His
625                 630                 635                 640

CAG CTG CGA TGC AAC GGA GTG CTG GAG GGT ATC CGC ATC TGT AGG AAG      1968
Gln Leu Arg Cys Asn Gly Val Leu Glu Gly Ile Arg Ile Cys Arg Lys
                645                 650                 655

GGC TTC CCC AAC CGC ATT CTT TAT GGG GAC TTC CGG CAG AGG TAT CGA      2016
Gly Phe Pro Asn Arg Ile Leu Tyr Gly Asp Phe Arg Gln Arg Tyr Arg
                660                 665                 670

ATC CTG AAC CCA GCA GCC ATC CCT GAG GGC CAA TTC ATT GAT AGC GGG      2064
Ile Leu Asn Pro Ala Ala Ile Pro Glu Gly Gln Phe Ile Asp Ser Gly
            675                 680                 685

AAA GGG GCT GAG AAG CTG CTG GGC TCC CTG GAC ATT GAC CAC AAC CAG      2112
Lys Gly Ala Glu Lys Leu Leu Gly Ser Leu Asp Ile Asp His Asn Gln
        690                 695                 700

TAC AAG TTT GGC CAC ACC AAG GTG TTC TTC AAG GCG GGG CTG CTG GGG      2160
Tyr Lys Phe Gly His Thr Lys Val Phe Phe Lys Ala Gly Leu Leu Gly
705                 710                 715                 720

CTG CTG GAG GAG ATG CGA GAT GAG AGG CTG AGC CGC ATC ATC ACC AGA      2208
Leu Leu Glu Glu Met Arg Asp Glu Arg Leu Ser Arg Ile Ile Thr Arg
                725                 730                 735

ATC CAG GCT CAA GCC CGA GGC CAG CTC ATG CGC ATT GAG TTC AAG AAG      2256
Ile Gln Ala Gln Ala Arg Gly Gln Leu Met Arg Ile Glu Phe Lys Lys
                740                 745                 750

ATG GTG GAG CGC AGG GAC GCC CTG CTG GTT ATC CAG TGG AAC ATC CGC      2304
Met Val Glu Arg Arg Asp Ala Leu Leu Val Ile Gln Trp Asn Ile Arg
            755                 760                 765

GCC TTC ATG GGG GTC AAG AAT TGG CCG TGG ATG AAG CTC TAC TTC AAG      2352
Ala Phe Met Gly Val Lys Asn Trp Pro Trp Met Lys Leu Tyr Phe Lys
770                 775                 780

ATC AAG CCG CTG CTG AAG AGC GCA GAG ACA GAG AAG GAG ATG GCC AAC      2400
Ile Lys Pro Leu Leu Lys Ser Ala Glu Thr Glu Lys Glu Met Ala Asn
785                 790                 795                 800

ATG AAA GAG GAG TTC GGG CGA GTC AAA GAT GCA CTA GAG AAG TCT GAG      2448
Met Lys Glu Glu Phe Gly Arg Val Lys Asp Ala Leu Glu Lys Ser Glu
                805                 810                 815

GCT CGC CGC AAG GAG CTG GAG GAG AAG ATG GTG TCC CTG CTG CAG GAG      2496
Ala Arg Arg Lys Glu Leu Glu Glu Lys Met Val Ser Leu Leu Gln Glu
            820                 825                 830

AAG AAT GAC CTG CAG CTC CAA GTG CAG GCG GAA CAA GAC AAC CTG GCA      2544
Lys Asn Asp Leu Gln Leu Gln Val Gln Ala Glu Gln Asp Asn Leu Ala
```

-continued

```
          835                 840                 845

GAT GCC GAG GAG CGC TGC GAC CAG CTG ATC AAG AAC AAG ATC CAG CTG          2592
Asp Ala Glu Glu Arg Cys Asp Gln Leu Ile Lys Asn Lys Ile Gln Leu
        850                 855                 860

GAG GCC AAG GTG AAG GAG ATG ACC GAG AGG CTG GAG GAC GAG GAG GAG          2640
Glu Ala Lys Val Lys Glu Met Thr Glu Arg Leu Glu Asp Glu Glu Glu
865                 870                 875                 880

ATG AAC GCC GAG CTC ACG GCC AAG AAG CGC AAG CTG GAA GAC GAG TGC          2688
Met Asn Ala Glu Leu Thr Ala Lys Lys Arg Lys Leu Glu Asp Glu Cys
                885                 890                 895

TCA GAG CTC AAG AAA GAT ATC GAT GAC CTG GAG CTG ACC CTG GCC AAG          2736
Ser Glu Leu Lys Lys Asp Ile Asp Asp Leu Glu Leu Thr Leu Ala Lys
        900                 905                 910

GTG GAG AAG GAA AAG CAC GCA ACA GAG AAC AAG GTT AAA AAC CTG ACA          2784
Val Glu Lys Glu Lys His Ala Thr Glu Asn Lys Val Lys Asn Leu Thr
        915                 920                 925

GAG GAG ATG GCC GGG CTG GAC GAG ATC ATT GCC AAG CTG ACC AAG GAG          2832
Glu Glu Met Ala Gly Leu Asp Glu Ile Ile Ala Lys Leu Thr Lys Glu
        930                 935                 940

AAG AAA GCT CTT CAA GAG GCC CAC CAG CAA GCC CTA GAT GAC CTT CAG          2880
Lys Lys Ala Leu Gln Glu Ala His Gln Gln Ala Leu Asp Asp Leu Gln
945                 950                 955                 960

GCT GAG GAA GAC AAG GTC AAC ACA CTG ACC AAG TCT AAA GTC AAG CTG          2928
Ala Glu Glu Asp Lys Val Asn Thr Leu Thr Lys Ser Lys Val Lys Leu
                965                 970                 975

GAG CAG CAG GTG GAT GAT CTG GAG GGA TCC CTG GAG CAG GAG AAG AAG          2976
Glu Gln Gln Val Asp Asp Leu Glu Gly Ser Leu Glu Gln Glu Lys Lys
        980                 985                 990

GTG CGC ATG GAC CTG GAG CGA GCA AAG CGG AAG CTG GAG GGT GAC CTG          3024
Val Arg Met Asp Leu Glu Arg Ala Lys Arg Lys Leu Glu Gly Asp Leu
        995                 1000                1005

AAG CTG ACC CAG GAG AGC ATC ATG GAC CTG GAG AAC GAC AAG CTT CAG          3072
Lys Leu Thr Gln Glu Ser Ile Met Asp Leu Glu Asn Asp Lys Leu Gln
        1010                1015                1020

CTG GAG GAA AAG CTC AAG AAG AAA GAG TTT GAC ATC AGT CAG CAG AAC          3120
Leu Glu Glu Lys Leu Lys Lys Lys Glu Phe Asp Ile Ser Gln Gln Asn
1025                1030                1035                1040

AGT AAA ATA GAG GAC GAG CAG GCC CTG GCC CTT CAG CTG CAG AAG AAA          3168
Ser Lys Ile Glu Asp Glu Gln Ala Leu Ala Leu Gln Leu Gln Lys Lys
                1045                1050                1055

CTG AAG GAA AAC CAG GCA CGC ATC GAG GAG CTG GAG GAG GAG CTA GAG          3216
Leu Lys Glu Asn Gln Ala Arg Ile Glu Glu Leu Glu Glu Glu Leu Glu
        1060                1065                1070

GCG GAG CGC ACA GCC CGG GCC AAG GTG GAG AAG CTG CGC TCA GAC CTG          3264
Ala Glu Arg Thr Ala Arg Ala Lys Val Glu Lys Leu Arg Ser Asp Leu
        1075                1080                1085

ACC CGG GAG CTG GAG GAG ATC AGT GAG AGG CTA GAG GAA GCC GGT GGG          3312
Thr Arg Glu Leu Glu Glu Ile Ser Glu Arg Leu Glu Glu Ala Gly Gly
        1090                1095                1100

GCC ACA TCT GTG CAG ATA GAG ATG AAC AAG AAG CGC GAG GCC GAG TTC          3360
Ala Thr Ser Val Gln Ile Glu Met Asn Lys Lys Arg Glu Ala Glu Phe
1105                1110                1115                1120

CAG AAG ATG CGG CGG GAC CTG GAG GAA GCC ACG CTG CAG CAT GAG GCC          3408
Gln Lys Met Arg Arg Asp Leu Glu Glu Ala Thr Leu Gln His Glu Ala
                1125                1130                1135

ACA GCC GCG GCC CTG CGC AAG AAG CAC GCA GAC AGC GTG GCC GAG CTG          3456
Thr Ala Ala Ala Leu Arg Lys Lys His Ala Asp Ser Val Ala Glu Leu
        1140                1145                1150

GGC GAG CAG ATA GAC AAT CTA CAG CGG GTG AAG CAG AAG CTG GAG AAA          3504
```

```
              Gly Glu Gln Ile Asp Asn Leu Gln Arg Val Lys Gln Lys Leu Glu Lys
                      1155                1160                1165

GAG AAG AGC GAG TTC AAA CTG GAG CTG GAT GAC GTC ACC TCT CAC ATG              3552
Glu Lys Ser Glu Phe Lys Leu Glu Leu Asp Asp Val Thr Ser His Met
        1170                1175                1180

GAG CAG ATC ATC AAG GCC AAG GCA AAC CTG GAG AAA GTG TCC CGG ACA              3600
Glu Gln Ile Ile Lys Ala Lys Ala Asn Leu Glu Lys Val Ser Arg Thr
1185                1190                1195                1200

CTG GAG GAC CAG GCG AAT GAA TAC CGG GTG AAG TTG GAA GAA GCC CAG              3648
Leu Glu Asp Gln Ala Asn Glu Tyr Arg Val Lys Leu Glu Glu Ala Gln
                1205                1210                1215

CGC TCC CTC AAT GAC TTC ACC ACA CAG CGA GCC AAG CTG CAG ACA GAG              3696
Arg Ser Leu Asn Asp Phe Thr Thr Gln Arg Ala Lys Leu Gln Thr Glu
                    1220                1225                1230

AAT GGC GAG TTG GCT AGG CAA CTG GAA GAA AAG GAG GCA CTG ATT TGG              3744
Asn Gly Glu Leu Ala Arg Gln Leu Glu Glu Lys Glu Ala Leu Ile Trp
                        1235                1240                1245

CAG CTG ACC CGG GGC AAG CTC TCC TAT ACC CAG CAG ATG GAG GAC CTC              3792
Gln Leu Thr Arg Gly Lys Leu Ser Tyr Thr Gln Gln Met Glu Asp Leu
            1250                1255                1260

AAG AGG CAG CTG GAG GAG GAA GGC AAG GCC AAG AAT GCC TTG GCC CAC              3840
Lys Arg Gln Leu Glu Glu Glu Gly Lys Ala Lys Asn Ala Leu Ala His
1265                1270                1275                1280

GCA CTG CAG TCA GCC CGG CAT GAC TGC GAC CTG CTG CGG GAA CAG TAC              3888
Ala Leu Gln Ser Ala Arg His Asp Cys Asp Leu Leu Arg Glu Gln Tyr
                1285                1290                1295

GAA GAA GAA ATG GAG GCC AAG GCC GAG CTG CAG CGT GTC CTG TCC AAG              3936
Glu Glu Glu Met Glu Ala Lys Ala Glu Leu Gln Arg Val Leu Ser Lys
                    1300                1305                1310

GCC AAC TCA GAG GTG GCC CAG TGG AGG ACC AAG TAT GAG ACG GAC GCC              3984
Ala Asn Ser Glu Val Ala Gln Trp Arg Thr Lys Tyr Glu Thr Asp Ala
                        1315                1320                1325

ATA CAG AGG ACG GAG GAG CTG GAG GAA GCC AAG AAG AAG CTG GCT CAG              4032
Ile Gln Arg Thr Glu Glu Leu Glu Glu Ala Lys Lys Lys Leu Ala Gln
            1330                1335                1340

AGG CTT CAG GAT GCT GAG GAG GCA GTG GAG GCC GTC AAC GCC AAG TGC              4080
Arg Leu Gln Asp Ala Glu Glu Ala Val Glu Ala Val Asn Ala Lys Cys
1345                1350                1355                1360

TCC TCG CTG GAG AAG ACC AAG CAC AGG CTG CAG AAC GAG ATC GAG GAC              4128
Ser Ser Leu Glu Lys Thr Lys His Arg Leu Gln Asn Glu Ile Glu Asp
                1365                1370                1375

CTG ATG GTG GAT GTG GAG CGC TCC AAT GCG GCC GCC GCA GCC CTG GAC              4176
Leu Met Val Asp Val Glu Arg Ser Asn Ala Ala Ala Ala Ala Leu Asp
                    1380                1385                1390

AAA AAG CAG AGG AAC TTC GAC AAG ATC CTG GCT GAG TGG AAG CAG AAG              4224
Lys Lys Gln Arg Asn Phe Asp Lys Ile Leu Ala Glu Trp Lys Gln Lys
                        1395                1400                1405

TAT GAG GAG TCC CAG TCA GAG CTG GAG TCT TCC CAG AAG GAG GCG CGC              4272
Tyr Glu Glu Ser Gln Ser Glu Leu Glu Ser Ser Gln Lys Glu Ala Arg
            1410                1415                1420

TCC CTG AGC ACA GAG CTC TTC AAG CTC AAG AAT GCC TAT GAG GAG TCT              4320
Ser Leu Ser Thr Glu Leu Phe Lys Leu Lys Asn Ala Tyr Glu Glu Ser
1425                1430                1435                1440

CTG GAG CAC CTG GAG ACC TTC AAG CGG GAG AAC AAG AAC CTC CAG GAG              4368
Leu Glu His Leu Glu Thr Phe Lys Arg Glu Asn Lys Asn Leu Gln Glu
                1445                1450                1455

GAG ATC TCA GAC CTG ACT GAA CAG CTG GGA GAA GGG GGT AAA AAT GTG              4416
Glu Ile Ser Asp Leu Thr Glu Gln Leu Gly Glu Gly Gly Lys Asn Val
                    1460                1465                1470
```

-continued

```
CAC GAG CTG GAG AAG ATC CGC AAA CAG CTG GAG GTG GAG AAG CTG GAA       4464
His Glu Leu Glu Lys Ile Arg Lys Gln Leu Glu Val Glu Lys Leu Glu
        1475                1480                1485

CTG CAG TCA GCC CTG GAG GAG GCT GAG GCC TCC CTG GAG CAT GAG GAG       4512
Leu Gln Ser Ala Leu Glu Glu Ala Glu Ala Ser Leu Glu His Glu Glu
    1490                1495                1500

GGC AAG ATC CTC CGA GCC CAG CTG GAG TTC AAC CAG ATC AAG GCA GAG       4560
Gly Lys Ile Leu Arg Ala Gln Leu Glu Phe Asn Gln Ile Lys Ala Glu
1505                1510                1515                1520

ATC GAA AGG AAG CTG GCA GAG AAG GAC GAG GAG ATG GAG CAG GCC AAG       4608
Ile Glu Arg Lys Leu Ala Glu Lys Asp Glu Glu Met Glu Gln Ala Lys
        1525                1530                1535

CGC AAC CAC CTG CGG GTG GTG GAC TCC CTA CAG ACC TCC CTG GAT GCC       4656
Arg Asn His Leu Arg Val Val Asp Ser Leu Gln Thr Ser Leu Asp Ala
    1540                1545                1550

GAG ACA CGC AGC CGC AAC GAG GCC CTG CGG GTG AAG AAG AAG ATG GAG       4704
Glu Thr Arg Ser Arg Asn Glu Ala Leu Arg Val Lys Lys Lys Met Glu
        1555                1560                1565

GGC GAC CTC AAT GAG ATG GAG ATC CAG CTC AGT CAG GCC AAT AGA ATA       4752
Gly Asp Leu Asn Glu Met Glu Ile Gln Leu Ser Gln Ala Asn Arg Ile
    1570                1575                1580

GCC TCA GAG GCC CAG AAG CAC TTG AAG AAC GCC CAA GCC CAC TTG AAG       4800
Ala Ser Glu Ala Gln Lys His Leu Lys Asn Ala Gln Ala His Leu Lys
1585                1590                1595                1600

GAC ACC CAG CTC CAG CTG GAT GAC GCA GTC CGT GCC AAT GAC GAC CTG       4848
Asp Thr Gln Leu Gln Leu Asp Asp Ala Val Arg Ala Asn Asp Asp Leu
        1605                1610                1615

AAG GAG AAC ATC GCC ATC GTG GAG CGG CGC AAC ACC CTG CTG CAG GCG       4896
Lys Glu Asn Ile Ala Ile Val Glu Arg Arg Asn Thr Leu Leu Gln Ala
    1620                1625                1630

GAG CTG GAG GAG CTG CGG GCC GTG GTG GAG CAG ACA GAG CGG TCT CGG       4944
Glu Leu Glu Glu Leu Arg Ala Val Val Glu Gln Thr Glu Arg Ser Arg
        1635                1640                1645

AAG CTG GCA GAG CAG GAG CTG ATC GAG ACC AGC GAG CGG GTG CAG CTG       4992
Lys Leu Ala Glu Gln Glu Leu Ile Glu Thr Ser Glu Arg Val Gln Leu
    1650                1655                1660

CTG CAC TCC CAG AAC ACC AGC CTC ATC AAC CAG AAG AAG AAG ATG GAT       5040
Leu His Ser Gln Asn Thr Ser Leu Ile Asn Gln Lys Lys Lys Met Asp
1665                1670                1675                1680

GCA GAC CTC TCC CAG CTC CAG ACA GAG GTG GAG GAG GCG GTG CAG GAG       5088
Ala Asp Leu Ser Gln Leu Gln Thr Glu Val Glu Glu Ala Val Gln Glu
        1685                1690                1695

TGT AGG AAC GCA GAG GAG AAG GCC AAG AAG GCC ATC ACA GAT GCC GCC       5136
Cys Arg Asn Ala Glu Glu Lys Ala Lys Lys Ala Ile Thr Asp Ala Ala
    1700                1705                1710

ATG ATG GCC GAG GAG CTG AAG AAG GAG CAG GAC ACC AGC GCC CAC CTG       5184
Met Met Ala Glu Glu Leu Lys Lys Glu Gln Asp Thr Ser Ala His Leu
        1715                1720                1725

GAG CGC ATG AAG AAG AAC ATG GAG CAG ACC ATC AAG GAC CTG CAG CAC       5232
Glu Arg Met Lys Lys Asn Met Glu Gln Thr Ile Lys Asp Leu Gln His
        1730                1735                1740

CGG CTG GAC GAG GCA GAG CAG ATC GCC CTC AAG GGT GGC AAG AAG CAG       5280
Arg Leu Asp Glu Ala Glu Gln Ile Ala Leu Lys Gly Gly Lys Lys Gln
1745                1750                1755                1760

CTG CAG AAA CTG GAG GCC CGG GTC CGG GAG CTG GAG AAT GAG CTG GAG       5328
Leu Gln Lys Leu Glu Ala Arg Val Arg Glu Leu Glu Asn Glu Leu Glu
            1765                1770                1775

GCT GAG CAG AAG CGC AAT GCG GAG TCG GTG AAG GGC ATG AGG AAG AGC       5376
Ala Glu Gln Lys Arg Asn Ala Glu Ser Val Lys Gly Met Arg Lys Ser
        1780                1785                1790
```

-continued

```
GAG CGG CGC ATC AAG GAG CTC ACC TAC CAG ACA GAG GAA GAC AAG AAG    5424
Glu Arg Arg Ile Lys Glu Leu Thr Tyr Gln Thr Glu Glu Asp Lys Lys
        1795                1800                1805

AAC TTG GTG CGG CTG CAG GAC CTG GTG GAC AAG CTG CAG TTG AAG GTG    5472
Asn Leu Val Arg Leu Gln Asp Leu Val Asp Lys Leu Gln Leu Lys Val
    1810                1815                1820

AAG GCC TAC AAG CGC CAG GCT GAA GAG GCG GAG GAA CAG GCC AAC ACC    5520
Lys Ala Tyr Lys Arg Gln Ala Glu Glu Ala Glu Glu Gln Ala Asn Thr
1825                1830                1835                1840

AAC CTG TCC AAG TTC CGC AAG GTG CAG CAC GAG CTG GAT GAG GCA GAG    5568
Asn Leu Ser Lys Phe Arg Lys Val Gln His Glu Leu Asp Glu Ala Glu
                1845                1850                1855

GAG AGG GCG GAC ATT GCC GAG TCC CAG GTC AAC AAG CTG CGG GCC AAG    5616
Glu Arg Ala Asp Ile Ala Glu Ser Gln Val Asn Lys Leu Arg Ala Lys
            1860                1865                1870

AGC CGT GAC ATT GGC GCC AAG CAG AAA ATG CAC GAT GAG GAA TAA        5661
Ser Arg Asp Ile Gly Ala Lys Gln Lys Met His Asp Glu Glu *
        1875                1880                1885
```

(2) INFORMATION FOR SEQ ID NO:3:

(i) SEQUENCE CHARACTERISTICS:
      (A) LENGTH: 1886 amino acids
      (B) TYPE: amino acid
      (D) TOPOLOGY: linear (ii) MOLECULE TYPE: protein (xi) SEQUENCE DESCRIPTION: SEQ ID NO:3:

```
Met Thr Asp Ala Gln Met Ala Asp Phe Gly Ala Ala Arg Tyr Leu Arg
 1               5                  10                  15

Lys Ser Glu Lys Glu Arg Leu Glu Ala Gln Thr Arg Pro Phe Asp Ile
            20                  25                  30

Arg Thr Glu Cys Phe Val Pro Asp Lys Glu Tyr Val Lys Ala
        35                  40                  45

Lys Ile Val Ser Arg Glu Gly Gly Lys Val Thr Ala Glu Thr Glu Asn
    50                  55                  60

Gly Lys Thr Val Thr Val Lys Glu Asp Gln Val Met Gln Gln Asn Pro
65                  70                  75                  80

Pro Lys Phe Asp Lys Ile Glu Asp Met Ala Met Leu Thr Phe Leu His
                85                  90                  95

Glu Pro Ala Val Leu Tyr Asn Leu Lys Glu Arg Tyr Ala Ala Trp Met
            100                 105                 110

Ile Tyr Thr Tyr Ser Gly Leu Phe Cys Val Thr Val Asn Pro Tyr Lys
        115                 120                 125

Trp Leu Pro Val Tyr Asn Ala Glu Val Val Ala Ala Tyr Arg Gly Lys
    130                 135                 140

Lys Arg Ser Glu Ala Pro Pro His Ile Phe Ser Ile Ser Asp Asn Ala
145                 150                 155                 160

Tyr Gln Tyr Met Leu Thr Asp Arg Glu Asn Gln Ser Ile Leu Ile Thr
                165                 170                 175

Gly Glu Ser Gly Ala Gly Lys Thr Val Asn Thr Lys Arg Val Ile Gln
            180                 185                 190

Tyr Phe Ala Ser Ile Ala Ala Ile Gly Asp Arg Ser Lys Lys Asp Asn
        195                 200                 205

Pro Asn Ala Asn Lys Gly Thr Leu Glu Asp Gln Ile Ile Gln Ala Asn
    210                 215                 220
```

-continued

```
Pro Ala Leu Glu Ala Phe Gly Asn Ala Lys Thr Val Arg Asn Asp Asn
225                 230                 235                 240

Ser Ser Arg Phe Gly Lys Phe Ile Arg Ile His Phe Gly Ala Thr Gly
            245                 250                 255

Lys Leu Ala Ser Ala Asp Ile Glu Thr Tyr Leu Leu Glu Lys Ser Arg
            260                 265                 270

Val Ile Phe Gln Leu Lys Ala Glu Arg Asn Tyr His Ile Phe Tyr Gln
        275                 280                 285

Ile Leu Ser Asn Lys Lys Pro Glu Leu Leu Asp Met Leu Leu Val Thr
        290                 295                 300

Asn Asn Pro Tyr Asp Tyr Ala Phe Val Ser Gln Gly Glu Val Ser Val
305                 310                 315                 320

Ala Ser Ile Asp Asp Ser Glu Leu Leu Ala Thr Asp Ser Ala Phe
            325                 330                 335

Asp Val Leu Gly Phe Thr Ala Glu Glu Lys Ala Gly Val Tyr Lys Leu
            340                 345                 350

Thr Gly Ala Ile Met His Tyr Gly Asn Met Lys Phe Lys Gln Lys Gln
            355                 360                 365

Arg Glu Glu Gln Ala Glu Pro Asp Gly Thr Glu Asp Ala Asp Lys Ser
    370                 375                 380

Ala Tyr Leu Met Gly Leu Asn Ser Ala Asp Leu Leu Lys Gly Leu Cys
385                 390                 395                 400

His Pro Gln Val Lys Val Gly Asn Glu Tyr Val Thr Lys Gly Gln Ser
            405                 410                 415

Val Gln Gln Val Tyr Tyr Ser Ile Gly Ala Leu Ala Lys Ser Val Tyr
            420                 425                 430

Glu Lys Met Phe Asn Trp Met Val Thr Arg Ile Asn Ala Thr Leu Glu
            435                 440                 445

Thr Lys Gln Pro Arg Gln Tyr Phe Ile Gly Val Leu Asp Ile Ala Gly
    450                 455                 460

Phe Glu Ile Ser Ser Leu Pro His Leu Lys Leu Met Gly Ile Met Ser
465                 470                 475                 480

Ile Leu Glu Glu Glu Cys Met Phe Pro Lys Ala Thr Asp Met Thr Phe
            485                 490                 495

Lys Ala Lys Leu Tyr Asp Asn His Leu Gly Lys Ser Asn Asn Phe Gln
            500                 505                 510

Lys Pro Arg Asn Val Lys Gly Lys Gln Glu Ala His Phe Ser Leu Val
    515                 520                 525

His Tyr Ala Gly Thr Val Asp Tyr Asn Ile Leu Gly Trp Leu Glu Lys
    530                 535                 540

Asn Lys Asp Pro Leu Asn Glu Thr Val Val Gly Leu Tyr Gln Lys Ser
545                 550                 555                 560

Ser Leu Lys Leu Met Ala Thr Leu Phe Ser Thr Tyr Ala Ser Ala Asp
            565                 570                 575

Thr Gly Asp Ser Gly Lys Gly Lys Gly Lys Lys Gly Ser Ser
            580                 585                 590

Phe Gln Thr Val Ser Ala Leu His Arg Glu Asn Leu Asn Lys Leu Met
        595                 600                 605

Thr Asn Leu Arg Thr Thr His Pro His Phe Val Arg Cys Ile Ile Pro
    610                 615                 620

Asn Glu Arg Lys Ala Pro Gly Val Met Asp Asn Pro Leu Val Met His
625                 630                 635                 640

Gln Leu Arg Cys Asn Gly Val Leu Glu Gly Ile Arg Ile Cys Arg Lys
```

```
                    645                 650                 655
Gly Phe Pro Asn Arg Ile Leu Tyr Gly Asp Phe Arg Gln Arg Tyr Arg
                660                 665                 670
Ile Leu Asn Pro Ala Ala Ile Pro Glu Gly Gln Phe Ile Asp Ser Gly
                675                 680                 685
Lys Gly Ala Glu Lys Leu Leu Gly Ser Leu Asp Ile Asp His Asn Gln
                690                 695                 700
Tyr Lys Phe Gly His Thr Lys Val Phe Phe Lys Ala Gly Leu Leu Gly
705                 710                 715                 720
Leu Leu Glu Glu Met Arg Asp Glu Arg Leu Ser Arg Ile Ile Thr Arg
                    725                 730                 735
Ile Gln Ala Gln Ala Arg Gly Gln Leu Met Arg Ile Glu Phe Lys Lys
                740                 745                 750
Met Val Glu Arg Arg Asp Ala Leu Leu Val Ile Gln Trp Asn Ile Arg
                755                 760                 765
Ala Phe Met Gly Val Lys Asn Trp Pro Trp Met Lys Leu Tyr Phe Lys
770                 775                 780
Ile Lys Pro Leu Leu Lys Ser Ala Glu Thr Glu Lys Glu Met Ala Asn
785                 790                 795                 800
Met Lys Glu Glu Phe Gly Arg Val Lys Asp Ala Leu Glu Lys Ser Glu
                    805                 810                 815
Ala Arg Arg Lys Glu Leu Glu Glu Lys Met Val Ser Leu Leu Gln Glu
                820                 825                 830
Lys Asn Asp Leu Gln Leu Gln Val Gln Ala Glu Gln Asp Asn Leu Ala
                835                 840                 845
Asp Ala Glu Glu Arg Cys Asp Gln Leu Ile Lys Asn Lys Ile Gln Leu
850                 855                 860
Glu Ala Lys Val Lys Glu Met Thr Glu Arg Leu Glu Asp Glu Glu Glu
865                 870                 875                 880
Met Asn Ala Glu Leu Thr Ala Lys Lys Arg Lys Leu Glu Asp Glu Cys
                    885                 890                 895
Ser Glu Leu Lys Lys Asp Ile Asp Asp Leu Glu Leu Thr Leu Ala Lys
                900                 905                 910
Val Glu Lys Glu Lys His Ala Thr Glu Asn Lys Val Lys Asn Leu Thr
                915                 920                 925
Glu Glu Met Ala Gly Leu Asp Glu Ile Ile Ala Lys Leu Thr Lys Glu
                930                 935                 940
Lys Lys Ala Leu Gln Glu Ala His Gln Gln Ala Leu Asp Asp Leu Gln
945                 950                 955                 960
Ala Glu Glu Asp Lys Val Asn Thr Leu Thr Lys Ser Lys Val Lys Leu
                    965                 970                 975
Glu Gln Gln Val Asp Asp Leu Glu Gly Ser Leu Glu Gln Glu Lys Lys
                980                 985                 990
Val Arg Met Asp Leu Glu Arg Ala Lys Arg Lys Leu Glu Gly Asp Leu
                995                 1000                1005
Lys Leu Thr Gln Glu Ser Ile Met Asp Leu Glu Asn Asp Lys Leu Gln
        1010                1015                1020
Leu Glu Glu Lys Leu Lys Lys Lys Glu Phe Asp Ile Ser Gln Gln Asn
1025                1030                1035                1040
Ser Lys Ile Glu Asp Glu Gln Ala Leu Ala Leu Gln Leu Gln Lys Lys
                    1045                1050                1055
Leu Lys Glu Asn Gln Ala Arg Ile Glu Glu Leu Glu Glu Glu Leu Glu
                1060                1065                1070
```

-continued

```
Ala Glu Arg Thr Ala Arg Ala Lys Val Glu Lys Leu Arg Ser Asp Leu
            1075                1080                1085
Thr Arg Glu Leu Glu Glu Ile Ser Arg Leu Glu Glu Ala Gly Gly
    1090                1095                1100
Ala Thr Ser Val Gln Ile Glu Met Asn Lys Lys Arg Glu Ala Glu Phe
1105                1110                1115                1120
Gln Lys Met Arg Arg Asp Leu Glu Glu Ala Thr Leu Gln His Glu Ala
                1125                1130                1135
Thr Ala Ala Leu Arg Lys Lys His Ala Asp Ser Val Ala Glu Leu
            1140                1145                1150
Gly Glu Gln Ile Asp Asn Leu Gln Arg Val Lys Gln Lys Leu Glu Lys
            1155                1160                1165
Glu Lys Ser Glu Phe Lys Leu Glu Leu Asp Asp Val Thr Ser His Met
    1170                1175                1180
Glu Gln Ile Ile Lys Ala Lys Ala Asn Leu Glu Lys Val Ser Arg Thr
1185                1190                1195                1200
Leu Glu Asp Gln Ala Asn Glu Tyr Arg Val Lys Leu Glu Glu Ala Gln
                1205                1210                1215
Arg Ser Leu Asn Asp Phe Thr Thr Gln Arg Ala Lys Leu Gln Thr Glu
            1220                1225                1230
Asn Gly Glu Leu Ala Arg Gln Leu Glu Glu Lys Glu Ala Leu Ile Trp
            1235                1240                1245
Gln Leu Thr Arg Gly Lys Leu Ser Tyr Thr Gln Gln Met Glu Asp Leu
    1250                1255                1260
Lys Arg Gln Leu Glu Glu Glu Gly Lys Ala Lys Asn Ala Leu Ala His
1265                1270                1275                1280
Ala Leu Gln Ser Ala Arg His Asp Cys Asp Leu Leu Arg Glu Gln Tyr
                1285                1290                1295
Glu Glu Glu Met Glu Ala Lys Ala Glu Leu Gln Arg Val Leu Ser Lys
            1300                1305                1310
Ala Asn Ser Glu Val Ala Gln Trp Arg Thr Lys Tyr Glu Thr Asp Ala
            1315                1320                1325
Ile Gln Arg Thr Glu Glu Leu Glu Glu Ala Lys Lys Lys Leu Ala Gln
    1330                1335                1340
Arg Leu Gln Asp Ala Glu Glu Ala Val Glu Ala Val Asn Ala Lys Cys
1345                1350                1355                1360
Ser Ser Leu Glu Lys Thr Lys His Arg Leu Gln Asn Glu Ile Glu Asp
                1365                1370                1375
Leu Met Val Asp Val Glu Arg Ser Asn Ala Ala Ala Ala Ala Leu Asp
            1380                1385                1390
Lys Lys Gln Arg Asn Phe Asp Lys Ile Leu Ala Glu Trp Lys Gln Lys
            1395                1400                1405
Tyr Glu Glu Ser Gln Ser Glu Leu Glu Ser Ser Gln Lys Glu Ala Arg
    1410                1415                1420
Ser Leu Ser Thr Glu Leu Phe Lys Leu Lys Asn Ala Tyr Glu Glu Ser
1425                1430                1435                1440
Leu Glu His Leu Glu Thr Phe Lys Arg Glu Asn Lys Asn Leu Gln Glu
                1445                1450                1455
Glu Ile Ser Asp Leu Thr Glu Gln Leu Gly Glu Gly Gly Lys Asn Val
            1460                1465                1470
His Glu Leu Glu Lys Ile Arg Lys Gln Leu Glu Val Glu Lys Leu Glu
            1475                1480                1485
```

-continued

```
Leu Gln Ser Ala Leu Glu Glu Ala Glu Ala Ser Leu Glu His Glu Glu
    1490                1495                1500
Gly Lys Ile Leu Arg Ala Gln Leu Glu Phe Asn Gln Ile Lys Ala Glu
1505                1510                1515                1520
Ile Glu Arg Lys Leu Ala Glu Lys Asp Glu Glu Met Glu Gln Ala Lys
                1525                1530                1535
Arg Asn His Leu Arg Val Val Asp Ser Leu Gln Thr Ser Leu Asp Ala
            1540                1545                1550
Glu Thr Arg Ser Arg Asn Glu Ala Leu Arg Val Lys Lys Lys Met Glu
        1555                1560                1565
Gly Asp Leu Asn Glu Met Glu Ile Gln Leu Ser Gln Ala Asn Arg Ile
    1570                1575                1580
Ala Ser Glu Ala Gln Lys His Leu Lys Asn Ala Gln Ala His Leu Lys
1585                1590                1595                1600
Asp Thr Gln Leu Gln Leu Asp Asp Ala Val Arg Ala Asn Asp Asp Leu
                1605                1610                1615
Lys Glu Asn Ile Ala Ile Val Glu Arg Arg Asn Thr Leu Leu Gln Ala
            1620                1625                1630
Glu Leu Glu Glu Leu Arg Ala Val Val Glu Gln Thr Glu Arg Ser Arg
        1635                1640                1645
Lys Leu Ala Glu Gln Glu Leu Ile Glu Thr Ser Glu Arg Val Gln Leu
    1650                1655                1660
Leu His Ser Gln Asn Thr Ser Leu Ile Asn Gln Lys Lys Lys Met Asp
1665                1670                1675                1680
Ala Asp Leu Ser Gln Leu Gln Thr Glu Val Glu Glu Ala Val Gln Glu
                1685                1690                1695
Cys Arg Asn Ala Glu Glu Lys Ala Lys Lys Ala Ile Thr Asp Ala Ala
            1700                1705                1710
Met Met Ala Glu Glu Leu Lys Lys Glu Gln Asp Thr Ser Ala His Leu
        1715                1720                1725
Glu Arg Met Lys Lys Asn Met Glu Gln Thr Ile Lys Asp Leu Gln His
    1730                1735                1740
Arg Leu Asp Glu Ala Glu Gln Ile Ala Leu Lys Gly Gly Lys Lys Gln
1745                1750                1755                1760
Leu Gln Lys Leu Glu Ala Arg Val Arg Glu Leu Glu Asn Glu Leu Glu
                1765                1770                1775
Ala Glu Gln Lys Arg Asn Ala Glu Ser Val Lys Gly Met Arg Lys Ser
            1780                1785                1790
Glu Arg Arg Ile Lys Glu Leu Thr Tyr Gln Thr Glu Glu Asp Lys Lys
        1795                1800                1805
Asn Leu Val Arg Leu Gln Asp Leu Val Asp Lys Leu Gln Leu Lys Val
    1810                1815                1820
Lys Ala Tyr Lys Arg Gln Ala Glu Glu Ala Glu Glu Gln Ala Asn Thr
1825                1830                1835                1840
Asn Leu Ser Lys Phe Arg Lys Val Gln His Glu Leu Asp Glu Ala Glu
                1845                1850                1855
Glu Arg Ala Asp Ile Ala Glu Ser Gln Val Asn Lys Leu Arg Ala Lys
            1860                1865                1870
Ser Arg Asp Ile Gly Ala Lys Gln Lys Met His Asp Glu Glu
        1875                1880                1885
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A transgenic mouse useful for studying congestive heart failure, said transgenic mouse being at least about five months old and having incorporated into its genome a transgene comprising:
    (a) a heart tissue-specific promoter selected from the group consisting of mouse and rat α myosin heavy chain promoters; and
    (b) a nucleic acid sequence encoding an amino acid sequence of a mammalian α myosin heavy chain protein, said nucleic acid sequence having a first mutation comprising a point mutation which results in an Arg403Gln mutation in said amino acid sequence and a second mutation comprising an in-frame deletion of the portion of said nucleic acid sequence that encodes amino acids 468–527 of the actin binding domain bridged by an addition of a nucleic acid sequence encoding eight amino acid residues that do not encode a portion of said actin binding domain;
    wherein said transgene is expressed in the heart tissues of said transgenic mouse so that said transgenic mouse exhibits at least one phenotypic characteristic associated with congestive heart failure if it is a male.

2. The transgenic mouse of claim 1, wherein said addition of amino acid residues is represented by amino acid sequence SEQ ID NO:1.

3. The transgenic mouse of claim 1, wherein said nucleic acid sequence is SEQ ID NO:2.

4. The transgenic mouse of claim 1, wherein said amino acid sequence is SEQ ID NO:3.

5. The transgenic mouse of claim 1, wherein said heart tissue-specific promoter is a rat α myosin heavy chain promoter.

6. The transgenic mouse of claim 1, wherein said nucleic acid sequence further comprises an intron 5' to the encoding sequence and an intron 3' to the encoding and polyadenylation sequences.

7. The transgenic mouse of claim 1, wherein said α myosin heavy chain protein is from a rodent α myosin heavy chain selected from the group consisting of a rat and a mouse.

8. The transgenic mouse of claim 1, wherein said mouse is male.

9. The transgenic mouse of claim 1, wherein said mouse exhibits dilation of at least one heart chamber.

10. The transgenic mouse of claim 9, wherein said heart chamber is the left ventricle.

11. The transgenic mouse of claim 9, wherein said mouse has a left ventricular end-diastolic dimension (LVEDD) of between about 2.7 mm and about 4.0 mm.

12. The transgenic mouse of claim 9, wherein said mouse has heart walls that are at least about 10% thinner than heart walls of a mouse that does not carry said transgene.

13. The transgenic mouse of claim 9, wherein said mouse has heart walls that are at least 30% thinner than heart walls of a mouse that does not carry said transgene.

14. The transgenic mouse of claim 9, wherein said mouse has heart walls that are at least 50% thinner than heart walls of a mouse that does not carry said transgene.

15. The transgenic mouse of claim 9, wherein said mouse has heart walls that are at least 70% thinner than heart walls of a mouse that does not carry said transgene.

16. The transgenic mouse of claim 9, wherein said mouse does not exhibit cardiac hypertrophy.

17. The transgenic mouse of claim 9, wherein said mouse has reduced systolic function compared to a mouse that does not carry said transgene.

18. The transgenic mouse of claim 9, wherein said mouse has a systolic dysfunction indicated by a percent fractional shortening (% FS) of between about % FS=18 and about % FS=30.

19. The transgenic mouse of claim 2 wherein said α myosin heavy chain protein is from a rat α myosin heavy chain.

20. A recombinant nucleic acid molecule comprising a nucleic acid sequence encoding an amino acid sequence of an α myosin heavy chain protein, said nucleic acid sequence having a first mutation comprising a point mutation which results in an Arg403Gln mutation in said amino acid sequence and a second mutation comprising an in-frame deletion of a portion of said nucleic acid sequence that encodes an actin binding domain;
    wherein said nucleic acid sequence is operatively linked to one or more expression control sequences.

21. The recombinant nucleic acid molecule of claim 20, wherein one of said expression control sequences is a heart tissue-specific promoter selected from the group consisting of mouse and rat α myosin heavy chain promoters.

22. The recombinant nucleic acid molecule of claim 21, wherein said heart tissue-specific promoter is a rat or mouse α myosin heavy chain promoter.

23. The recombinant nucleic acid molecule of claim 20, wherein said in-frame deletion comprises a deletion of said nucleic acid sequence encoding at least about 15 amino acids of said actin binding domain.

24. The recombinant nucleic acid molecule of claim 20, wherein said in-frame deletion comprises a deletion in said nucleic acid sequence that encodes amino acid residues from about position 468 to about position 527 of said actin binding domain.

25. The recombinant nucleic acid molecule of claim 20, wherein said in-frame deletion is bridged by a nucleic acid sequence encoding an addition of amino acid residues that do not encode a portion of said actin binding domain of said α myosin protein.

26. The recombinant nucleic acid molecule of claim 20, wherein said nucleic acid sequence is SEQ ID NO:2.

27. The recombinant nucleic acid molecule of claim 20, wherein said amino acid sequence is SEQ ID NO:3.

28. The recombinant nucleic molecule of claim 21, wherein said heart tissue-specific promoter is a mouse α myosin heavy chain promoter.

29. The recombinant nucleic acid molecule of claim 24, wherein said in-frame deletion comprises a deletion of said nucleic acid sequence encoding at least about 15 amino acid residues from about position 468 to about position 527 of said actin binding domain.

30. The recombinant nucleic acid molecule of claim 29, wherein said in-frame deletion comprises a deletion of said nucleic acid sequence encoding all of said amino acid residues from about position 468 to about position 527 of said actin binding domain.

31. The recombinant nucleic acid molecule of claim 30, wherein said in-frame deletion is bridged by a nucleic acid sequence encoding an addition of amino acid residues that do not encode a portion of said actin binding domain.

32. The recombinant nucleic acid molecule of claim 31, wherein said addition of amino acid residues comprises an amino acid sequence of about 8 amino acid residues.

33. The recombinant nucleic acid molecule of claim 32, wherein said addition of amino acid residues is represented by amino acid SEQ ID NO:1.

34. The recombinant nucleic acid molecule of claim 21, wherein said expression control sequences further include 5' and 3' flanking introns and polyadenylation sequences.

35. The recombinant nucleic acid molecule of claim 22, wherein said heart tissue-specific promoter is a rat α myosin heavy chain promoter.

36. A method of screening compounds to determine their usefulness for treating or preventing congestive heart failure, comprising the steps of:
  (a) providing a male transgenic mouse having incorporated into its genome a transgene comprising a heart tissue-specific promoter selected from the group consisting of mouse and rat α myosin heavy chain promoters, and a nucleic acid sequence encoding an amino acid sequence of a mammalian α myosin heavy chain protein, said nucleic acid having a first mutation comprising a point mutation which results in an Arg403Gln mutation in said amino acid sequence and a second mutation comprising an in-frame deletion of the portion of said nucleic acid sequence that encodes amino acids 468–527 of the actin binding domain bridged by an addition of a nucleic acid sequence encoding eight amino acid residues that do not encode a portion of said actin binding domain; wherein said transgene is expressed in the heart tissues of said transgenic mouse so that when said transgenic mouse is at least about five months old, it exhibits at least one phenotypic characteristic associated with congestive heart failure;
  (b) administering a compound to be evaluated to the male transgenic mouse; and
  (c) evaluating a change in a phenotypic characteristic associated with congestive heart failure in said transgenic mouse compared to another transgenic mouse that did not receive said compound to determine the efficacy of said compound in treating or preventing congestive heart failure.

37. A method for evaluating the effects of external factors selected from the group consisting of diet and exercise on congestive heart failure, comprising the steps of:
  (a) establishing a normal control regimen for an external factor selected from the group consisting of diet and exercise in a first male transgenic mouse having incorporated into its genome a transgene comprising a heart tissue-specific promoter selected from the group consisting of mouse and rat α myosin heavy chain promoters, and a nucleic acid sequence encoding an amino acid sequence of a mammalian α myosin heavy chain protein, said nucleic acid sequence having a first mutation comprising a point mutation which results in an Arg403Gln mutation in said amino acid sequence and a second mutation comprising an in-frame deletion of the portion of said nucleic acid sequence that encodes amino acids 468–527 of the actin binding domain bridged by an addition of a nucleic acid sequence encoding 8 amino acid residues that do not encode a portion of said actin binding domain;
  (b) modulating said regimen for said external factor in a second male transgenic mouse having the same transgene as said first transgenic mouse; and
  (c) monitoring said second transgenic mouse for a change in a phenotypic characteristic associated with congestive heart failure compared to said first transgenic mouse.

* * * * *